(12) United States Patent
Wong

(10) Patent No.: US 11,982,616 B2
(45) Date of Patent: May 14, 2024

(54) SPECTRALLY RESOLVED IMAGING FOR AGRICULTURAL PRODUCT ASSESSMENT

(71) Applicant: Headwall Photonics Inc., Bolton, MA (US)

(72) Inventor: Kwok-Keung Wong, Bolton, MA (US)

(73) Assignee: Headwall Photonics Inc., Bolton, MA (US)

(*) Notice: Subject to any disclaimer, the term of this patent is extended or adjusted under 35 U.S.C. 154(b) by 145 days.

(21) Appl. No.: 17/653,514

(22) Filed: Mar. 4, 2022

(65) Prior Publication Data

US 2022/0291120 A1 Sep. 15, 2022

Related U.S. Application Data

(60) Provisional application No. 63/158,666, filed on Mar. 9, 2021, provisional application No. 63/158,653, filed on Mar. 9, 2021.

(51) Int. Cl.
| | |
|---|---|
| *G01J 3/28* | (2006.01) |
| *G01N 21/31* | (2006.01) |
| *G01N 33/02* | (2006.01) |

(52) U.S. Cl.
CPC .......... *G01N 21/314* (2013.01); *G01J 3/2823* (2013.01); *G01N 33/025* (2013.01); *G01J 2003/2833* (2013.01); *G01J 2003/2836* (2013.01)

(58) Field of Classification Search
CPC ... G01N 21/314; G01N 33/025; G01J 3/2823; G01J 2003/2833; G01J 2003/2836; G01J 3/0218; G01J 3/13; G01J 3/18; G01J 3/28
See application file for complete search history.

(56) References Cited

U.S. PATENT DOCUMENTS

| | | |
|---|---|---|
| 6,266,140 B1 | 7/2001 | Xiang et al. |
| 6,839,136 B2 | 1/2005 | Mikes |
| 7,518,722 B2 | 4/2009 | Julian et al. |
| 10,048,100 B1 * | 8/2018 | Workman, Jr. ........ G01D 18/00 |
| 10,458,908 B2 * | 10/2019 | Yarden ................ G01N 21/359 |

(Continued)

OTHER PUBLICATIONS

Hall, David G. et al. "A Perspective of Research on HLB and its Vector in the United States". US Horticultural Research Laboratory, USDA-ARS, Ft Pierce, FL.

(Continued)

*Primary Examiner* — Abdullahi Nur
(74) *Attorney, Agent, or Firm* — Intrinsic Law Corp.

(57) ABSTRACT

A method for determining a quality condition of an agricultural product comprises: receiving a received light at a light detector, the received light comprising reflected, scattered, refracted, and/or deflected light from the agricultural product; transmitting the received light to a spectrometer; producing agricultural product (AP) spectral data of the received light using the spectrometer; with a computer in electrical communication with the spectrometer, comparing the AP spectral data to reference spectral data to determine whether the agricultural product has the quality condition, the reference spectral data corresponding to known quality conditions of the agricultural product; and with the computer, generating an output signal corresponding to the quality condition of the agricultural product.

8 Claims, 18 Drawing Sheets

(56) References Cited

U.S. PATENT DOCUMENTS

| | | | | |
|---|---|---|---|---|
| 2002/0024665 A1* | 2/2002 | Masten | ............. | G01N 21/31 |
| | | | | 356/328 |
| 2004/0149893 A1* | 8/2004 | Scott | ............. | A01B 79/005 |
| | | | | 250/221 |
| 2007/0231877 A1* | 10/2007 | Choate | ............. | C12M 45/04 |
| | | | | 210/601 |
| 2018/0077912 A1* | 3/2018 | Comparat | ............. | A01K 67/033 |
| 2019/0021646 A1 | 1/2019 | Bannon et al. | | |
| 2020/0320682 A1* | 10/2020 | Alexander | ............. | G06N 3/08 |

OTHER PUBLICATIONS

Neupane, Diwash et al. "Estimating Citrus Production Loss due to Citrus Huanglongbing in Florida". University of Florida. Feb. 6-9, 2016.

Zambrano, Ricardo Martinez. "Overview of the Citrus Industry in Mexico". Sheraton Sand Key Resort, Clearwater, FL. Sep. 21, 2016.

* cited by examiner

SPECTRALLY RESOLVED IMAGING FOR AGRICULTURAL PRODUCT ASSESSMENT

CROSS-REFERENCE TO RELATED APPLICATIONS

This application claims priority to U.S. Provisional Application No. 63/158,653, titled "Apparatus and Method Using Aerial Imaging for Spectral Analysis of Crops for a Condition," filed on Mar. 9, 2021, and to U.S. Provisional Application No. 63/158,666, titled "Apparatus and Method Using Assembly Line Imaging for Spectral Analysis of Agricultural Products for a Condition," filed on Mar. 9, 2021, which are hereby incorporated by reference.

TECHNICAL FIELD

This application relates generally to the detection of quality conditions in agricultural products using spectroscopy.

BACKGROUND

Existing quality detection systems for agricultural products rely on visual inspection, automated inspection using cameras in the visual spectrum (i.e., RGB cameras), or laboratory analyses. However, visual inspection is time-consuming and prone to human error. Cameras operating solely in the visual spectrum are inaccurate. While laboratory analyses are highly accurate, they take too long and are too expensive for large volumes.

It would be desirable to overcome one or more of these deficiencies.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a method for determining a quality condition of an agricultural product, comprising: receiving a received light at a light detector, the received light comprising reflected, scattered, refracted, and/or deflected light from the agricultural product; transmitting the received light to a spectrometer; producing agricultural product (AP) spectral data of the received light using the spectrometer; with a computer in electrical communication with the spectrometer, comparing the AP spectral data to reference spectral data to determine whether the agricultural product has the quality condition, the reference spectral data corresponding to known quality conditions of the agricultural product; and with the computer, generating an output signal corresponding to the quality condition of the agricultural product.

In one or more embodiments, the method further comprises sending the output signal to a display coupled to the computer. In one or more embodiments, the output signal includes a product sort output signal, and the method further comprises: sending the product sort output signal from the computer to an automated product sorter: and sorting the agricultural product based on the quality condition.

In one or more embodiments, the quality condition comprises an agricultural disease and the method further comprises discarding the agricultural product, with the product sorter, when the agricultural product has the agricultural disease. In one or more embodiments, the quality condition comprises a pathogen contaminating the agricultural product and the method further comprises discarding the agricultural product, with the product sorter, when the agricultural product has the pathogen. In one or more embodiments, the agricultural product comprises an orange and the quality condition comprises a Brix content of the orange. In one or more embodiments, the method further comprises comprising sorting the agricultural product, with the product sorter, when the Brix content is below a predetermined value.

In one or more embodiments, the received light includes wavelengths within a wavelength range of about 400 nm to about 1,000 nm. In one or more embodiments, the wavelength range is about 400 nm to about 700 nm. In one or more embodiments, the computer compares the AP spectral data to the reference spectral data using a mathematical regression algorithm. In one or more embodiments, the method further comprises directing a produced light onto the agricultural source from a light output, the light output spaced a predetermined distance from the light detector. In one or more embodiments, the produced light includes wavelengths within a wavelength range of about 400 nm to about 2,500 nm.

Another aspect of the invention is directed to a method for sorting an agricultural product, comprising: providing a relative movement between a light detector and an agricultural product; receiving a received light at a light detector, the received light comprising reflected, scattered, refracted, and/or deflected light from the agricultural product; transmitting the received light to a spectrometer; producing AP spectral data of the received light using the spectrometer; in a computer in electrical communication with the spectrometer, comparing the AP spectral data to reference spectral data to determine whether the agricultural product has the quality condition, the reference spectral data corresponding to known quality conditions of the agricultural product; when the exposed agricultural product has the quality condition: sending an output signal to an automated product sorter; and activating the product sorter based on the output signal.

In one or more embodiments, the agricultural product is located on a conveyor belt, and when the exposed agricultural product has the quality condition, the automated product sorter moves the agricultural product from the conveyor belt to a specified bin or secondary conveyor belt. In one or more embodiments, the agricultural product comprises an orange, the quality condition comprises a minimum Brix content, and the automated product sorter moves the agricultural product from the conveyor belt to the specified bin or secondary conveyor belt when the agricultural product has a measured Brix below the minimum Brix content.

In one or more embodiments, the quality condition comprises an agricultural disease, and the automated product sorter removes the agricultural product from the conveyor belt when the agricultural product has the agricultural disease. In one or more embodiments, the quality condition comprises a pathogen contaminating the agricultural product, and the automated product sorter removes the agricultural product from the conveyor belt when the agricultural product has the pathogen.

Yet another aspect of the invention is directed to a method for sorting an agricultural product, comprising: providing a relative movement between a light detector and a plurality of agricultural products disposed in a container in a vehicle; receiving a received light at a light detector, the received light comprising reflected, scattered, refracted, and/or deflected light from the agricultural product; transmitting the received light to a spectrometer; producing AP spectral data of the received light using the spectrometer; in a computer in electrical communication with the spectrometer, comparing the AP spectral data to reference spectral data to determine whether the agricultural products have a quality condition, the reference spectral data corresponding to known quality conditions of the agricultural product; when the exposed agricultural product has the quality condition: sending an output signal to an automated product sorter; and activating a gate to provide or restrict access to a direction of travel for the vehicle.

In one or more embodiments, the agricultural products comprise oranges, and the quality condition comprises a minimum Brix content of each orange. In one or more embodiments, the agricultural products comprise oranges, and the quality condition comprises a minimum average Brix content of the oranges. In one or more embodiments, the vehicle drives while the received light is received at the light detector. In one or more embodiments, the agricultural product is in vivo when the received light is received at the light detector. In one or more embodiments, the agricultural product has been harvested when the received light is received at the light detector.

In one or more embodiments, the agricultural product is illuminated by sunlight and/or moonlight. In one or more embodiments, the method further comprises illuminating the agricultural product with an artificial light produced by a halogen lamp, a light emitting diode, a laser, and/or a supercontinuum light source.

Another aspect of the invention is directed to a system comprising: a light detector; a spectrometer optically coupled to the light detector; an automated product sorter; and a computer electrically coupled to the spectrometer and to the product sorter, the computer having a processor and non-volatile memory operably coupled to the processor, the non-volatile memory storing computer-readable instructions that, when executed by the processor, cause the processor to: compare the AP spectral data to reference spectral data to determine whether the agricultural product has the quality condition, and when the agricultural product has the quality condition, generate an output signal that causes the product sorter to sort the agricultural product.

BRIEF DESCRIPTION OF THE DRAWINGS

For a fuller understanding of the nature and advantages of the present concepts, reference is made to the detailed description of preferred embodiments and the accompanying drawings.

DETAILED DESCRIPTION

Figure 1:
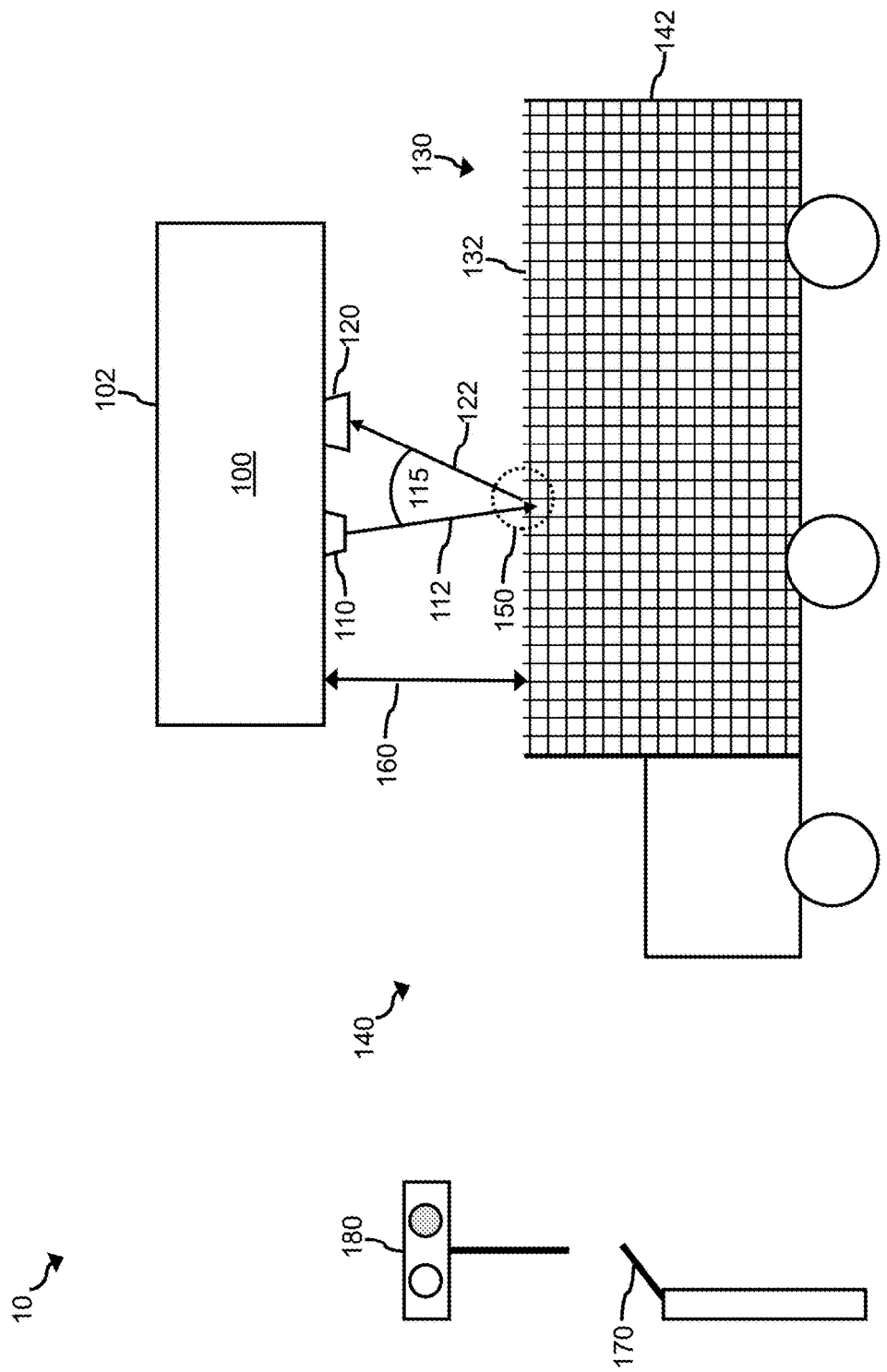
FIG. 1 is a schematic diagram of a quality condition detection system according to one or more embodiments.

FIG. 1 is a schematic diagram of a quality condition detection system 10 according to one or more embodiments. The quality condition detection system 10 includes a quality detection apparatus 100 having a housing 102 on which a light output 110 and a light detector 120 are disposed. The housing 102 can be mounted on a ceiling, a wall, or on a raised structure, so that the quality detection apparatus 100 is elevated with respect to the agricultural product 130.

Light 112 is emitted from light output 110 towards agricultural products 130, which can be carried in a truck 140 having an open bed 142 or open trailer, or in another vehicle. The light 112 can have a single wavelength or a wavelength range. The agricultural products 130 include exposed agricultural products 132 that have an at least partially unobstructed line-of-sight to the light output 110 to directly receive the light 112 from the light output 110.

In operation, the light 112 passes out of the light output 110 to scan the agricultural products 130. When one or more exposed agricultural products 132 passes through a target or focal location 150 of the light 112, the exposed agricultural product(s) scatters, refracts, and/or reflects at least a portion of the light 112, and at least some of the scattered, refracted, and/or reflected light 122 (in general, received light 122) is collected by the light detector 120 as one or more light images. The light 112 can provide the illuminance needed to perform the scan with quality detection apparatus 100 at a sufficient signal-to-noise ratio. The illuminance can be provided solely by the light output 110 or by a combination of light from the light output 110 and ambient light, which can be direct or indirect ambient light. In an embodiment, the illuminance provided by the light output 110 and/or by ambient light preferably provides at least about ⅓ sun illuminance (about 33,000 lux) incident upon the agricultural products 132. The light provided by the light output 110 can be focused to reduce the illumination of neighboring areas outside the perimeter or boundary of the sampling area, such as the open bed 142 in FIG. 1, which can reduce the effective signal-to-noise ratio. Illuminating the neighboring areas outside the perimeter or boundary of the sampling area can also waste energy and increase the operating costs of the quality condition detection system 10. The light output 110 preferably provides uniform or substantially uniform illumination over the full sampling area (e.g., the open bed 142). For example, the illumination provided by the light output 110 can preferably be spatially uniform for the entire sample of agricultural products 130 to prevent over- and/or under-representation of certain agricultural products in the quality assessment. Spectrally non-uniform illumination can obscure the comparison of measurements to reference spectra. In addition, the illumination provided by the light output 110 can preferably provide a consistent color content over time.

The light detector 120 can include lenses, mirrors, and optical filters to collect and condition the received light 122. In another embodiment, the light detector 120 can include optical fibers to collect the received light, for example as disclosed in U.S. Patent Application Publication No. 2019/0021646, which is hereby incorporated by reference. The quality detection apparatus 100 can analyze the collected or received light to determine if a spectral signature of a quality condition is present. The spectral signature can include one or more wavelengths or wavelength ranges where the relative intensity of the collected light is different when the exposed agricultural product 132 has a quality condition than when the exposed agricultural product 132 does not have the quality condition. The spectral signature and/or quality condition can be determined by comparing spectral data of the exposed agricultural product 132 with reference spectral data of agricultural products having known quality conditions. The quality detection apparatus 100 can include a spectrograph, one or more signal processors, and firmware and/or software stored on memory operably coupled to the signal processor(s). The output of quality detection apparatus 100 can comprise a multi-dimensional data file representing quantified spectral content at each pixel in a high-spatial-resolution image. The software can optionally convert the high-spatial-resolution image a simple yes/no result or a grade in a predefined quality scale.

The quality condition can comprise the ripeness, sweetness (e.g., sugar content such as Brix (e.g., ° Brix) sourness (e.g., limonin content), color, color variation, smoothness, roughness, imperfections, rottenness, or other quality condition of the agricultural products 130. Additionally or alternatively, the quality condition can comprise a disease. For example, the agricultural products 130 can include citrus fruits (e.g., oranges, grapefruits, lemons, limes, etc.) and the quality condition can include Huanglongbing (HLB) disease, also known as citrus greening disease. In another example, the agricultural products 130 can include coffee beans (e.g., green coffee beans) and the quality condition can include a defect in the coffee beans, such as full or partial black beans, full or partial sour beans, damaged beans, or unhulled beans. In yet another example, the agricultural products 130 can includes walnuts and the quality condition can include walnut blight (e.g., *Xanthomonas campestris*) and/or powdery mildew (e.g., *Phyllactinia guttata*). In another example, agricultural products 130 can include cranberries and the quality condition can include fruit rot (e.g., field rot) and/or cranberry overripening/rotting. In yet another example, the quality condition can be the ripening state (e.g., under-ripe and/or overripe) of the agricultural products 130. In yet another example, the agricultural products 130 can include raw meat and the quality condition can include undesirable bacteria in the raw meat. In a specific example, the raw meat can include chicken and the undesirable bacteria can include *Salmonella* bacteria. In another specific example, the raw meat can include beef and the undesirable bacteria can include *Salmonella, Escherichia coli (E. coli), Shigella, Staphylococcus aureus*, and/or *Listeria monocytogenes* bacteria.

A spectral angle 115 can be defined between a first axis along which the light 112 passes (e.g., the incidence angle of light 112) from the light output 110 and to the exposed agricultural product 132 and a second axis along which the received light 122 passes from the exposed agricultural product 132 to the light detector 120. The spectral angle 115 can vary as a function of the vertical distance 160 or height between the quality detection apparatus 100 and the exposed agricultural products 132. The spectral angle 115 is preferably set to be about the same as the spectral angle that was used to generate the reference spectral data. Each set of reference spectral data is preferably collected using the same or about the same spectral angle. In some embodiments, the height of the quality detection apparatus 100 can be adjusted to vary the spectral angle 115. For example, when the vertical distance 160 is different between trucks, the height of the quality detection apparatus 100 can be adjusted so that the spectral angle 115 remains the same or about the same for each truck. In some embodiments, the illumination source and/or the sensor light collection components can be statically or dynamically modified to vary the spectral angle 115. As used herein, "about" means plus or minus 10% of the relevant value.

In some embodiments, the quality condition detection system 10 operates in a light-controlled environment (e.g., to avoid interference from other light sources) so that it only collects light that originated from the light output 110, which is then refracted and/or deflected by the exposed agricultural product 132, as discussed above. For example, the quality condition detection system 10 can be disposed in a garage, a tent, a hangar, under a roof or awning, or in another light-controlled environment.

The quality detection apparatus 100 and the truck 140 can move with respect to each other. In one example, the quality detection apparatus 100 is stationary and the truck 140 drives forward so that all or substantially most of the exposed agricultural product 132 across the width of the open bed 142 is scanned (e.g., within the field of view of the light output 110 and light detector 120). The truck 140 can drive at a predetermined speed (e.g., about 5 mph) so that the scans are performed consistently across the length of the open bed 142. In another example, the quality detection apparatus 100 is mobile and the truck 140 is stationary. In this example, the quality detection apparatus 100 can electromechanically move along a wire or a track (e.g., a gantry system) to scan the length of the exposed agricultural product 132 in the open bed 142. The quality detection apparatus 100 can move at a predetermined speed (e.g., about 5 mph) so that the scans are performed consistently.

The quality detection apparatus 100 can generate an output signal that indicates whether a quality condition is detected or, alternatively, whether a quality condition is not detected. The output signal can cause an electromechanical gate 170 to open or close. In one example, a first output signal can cause a first electromechanical gate 170 to open that can cause the truck 140 to travel in a first direction (e.g., to discard the agricultural products 130 if the quality condition is poor) and can cause a second electromechanical gate 170 to close to prevent the truck from travelling in a second direction, such as to a factory to process the agricultural products 130. A second output signal can cause the second electromechanical gate 170 to open that can cause the truck 140 to travel in the second direction and can cause the first electromechanical gate 170 to close to prevent the truck from travelling in the first direction.

Additionally or alternatively, the output signal from the quality detection apparatus 100 can cause a light 180 to change color or state. The light 180 can indicate whether the quality condition of the agricultural products is good or poor. For example, one color (e.g., green) of the light 180 can indicate that the quality condition is good. Another color (e.g., red) of the light 180 can indicate that the quality condition is poor. The light 180 can indicate the quality condition of the agricultural product from within a set of graded categories (e.g. poor, low, better, best). The light 180 can indicate a direction for the truck 140 to travel after the scan instead of or in addition to the electromechanical gate(s) 170.

The electromechanical gate(s) 170 and the light 180 can be in wired or wireless communication with the quality detection apparatus 100.

Figure 2:
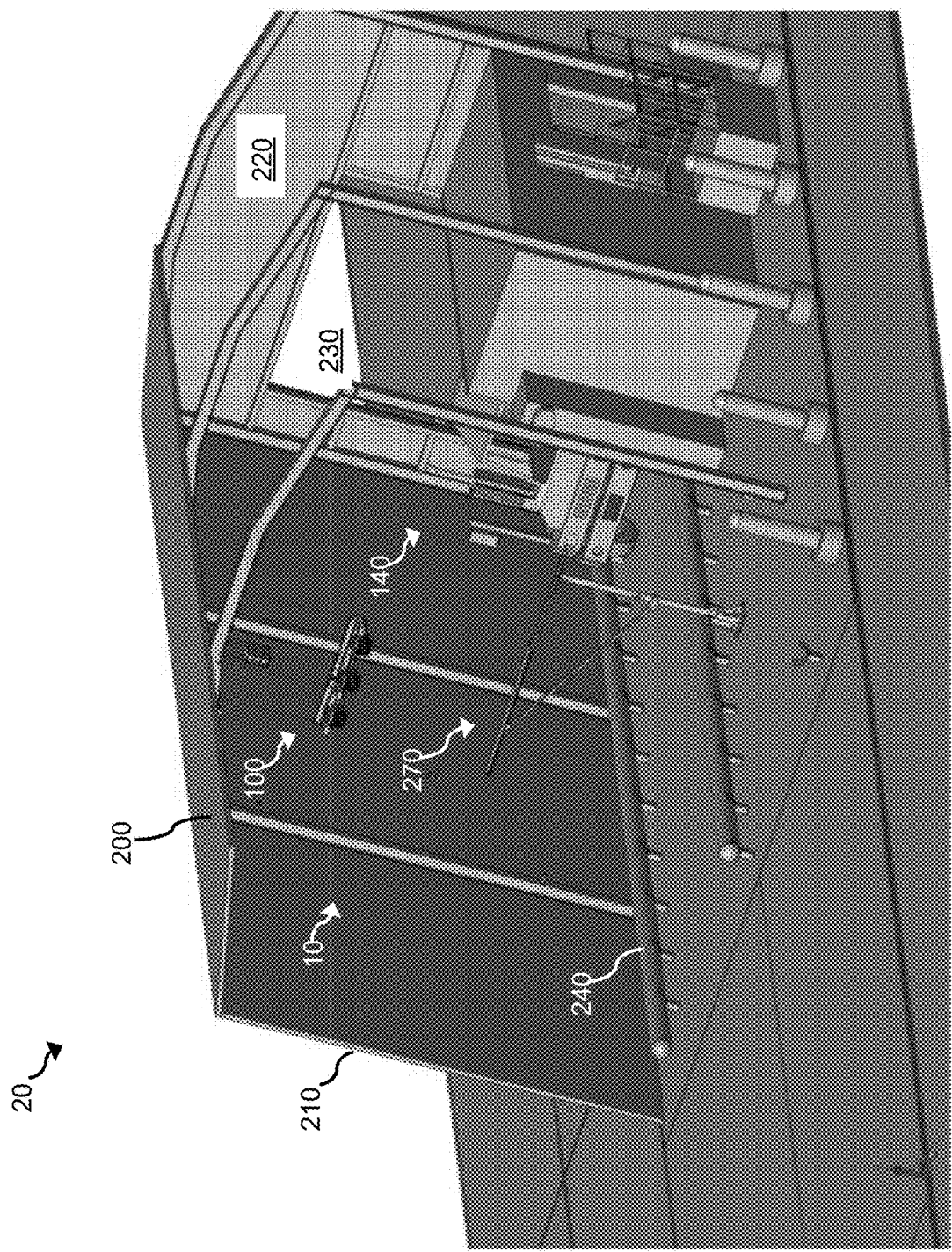
FIG. 2 is a perspective view of a partially-enclosed environment in which the quality condition detection system of FIG. 1 can be used.

FIG. 2 is a perspective view of a partially-enclosed environment 20 in which the quality condition detection system 10 can be used. The partially-enclosed environment 20 is similar to a hangar or a garage. For example, the partially-enclosed environment 20 includes a roof 200, sidewalls 210, and front and rear walls 220. To show the interior the partially-enclosed environment 20, only a portion of the roof 200, only one sidewall 210, and only the front wall 220 is illustrated. The front and rear walls 220 have openings 230 that are sized to allow a truck 140 to drive through and into the partially-enclosed environment 20. In operation, the truck 140 stops at a gate 270, which can be a manual or an electromechanical gate. The gate 270 is positioned so that the exposed agricultural product 132 in the open bed 142 is not within the field of view of the quality detection apparatus 100. To begin the scan, the gate 270 is opened and the truck 140 can drive forward at a predetermined speed (e.g., about 5 mph). Elevated rails 240 can be placed above the road surface to force the driver to drive straight. Alternatively, the scan can begin when the gate 270 is closed and the quality detection apparatus 100 can move towards the back of the truck at a predetermined speed (e.g., about 5 mph).

Figure 3:
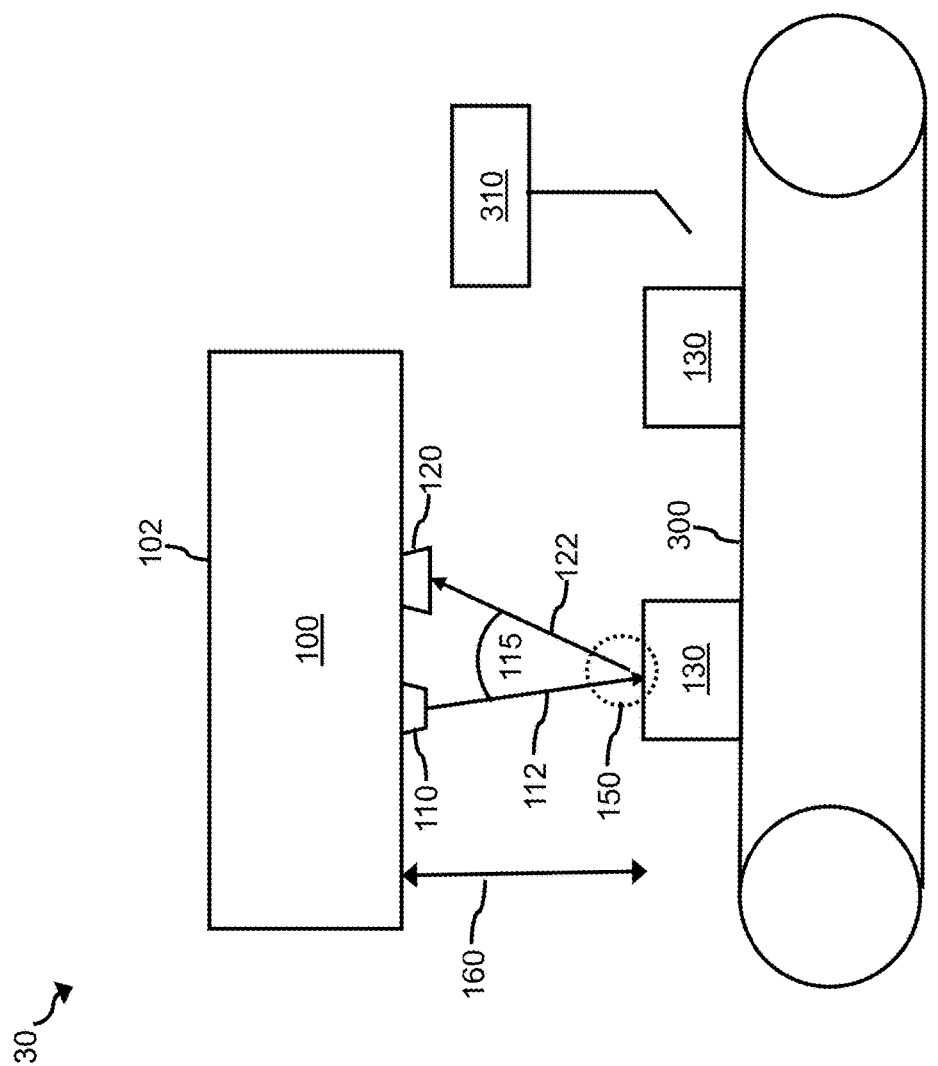
FIG. 3 is a block diagram of a quality condition detection system according to another embodiment.

FIG. 3 is a block diagram of a quality condition detection system 30 according to another embodiment. Quality condition detection system 30 can be the same as condition detection system 10 except that quality detection system 30 is configured to detect a quality condition of agricultural products 130 as they move along a conveyor belt 300. The quality detection system 30 can include an automated product sorter 310 that can remove agricultural products 130 from the conveyor belt 300 based on an output signal from the quality detection apparatus 100. For example, the automated product sorter 310 can remove agricultural products 130 that have a poor quality condition or that have a good quality condition from the conveyor belt 300. Additionally or alternatively, the automated product sorter 310 can sort the agricultural products 130 based on and/or using the detected quality condition(s). For the example, the automated product sorter 310 can sort (e.g., transfer or move) the agricultural products 130 into different bins that can be dedicated for respective quality condition(s) (e.g., a first bin for a first (e.g., good) quality condition and a second bin for a second (e.g., poor) quality condition). In another example, the automated product sorter 310 can sort the agricultural products 130 onto a secondary conveyor belt based on and/or using the detected quality condition(s). In an embodiment, agricultural products 130 having a first (e.g., good) quality condition can remain on the primary or main conveyor belt and agricultural products 130 having a second (e.g., poor) quality condition can be moved to the secondary conveyor belt (or vice versa).

Figure 4:
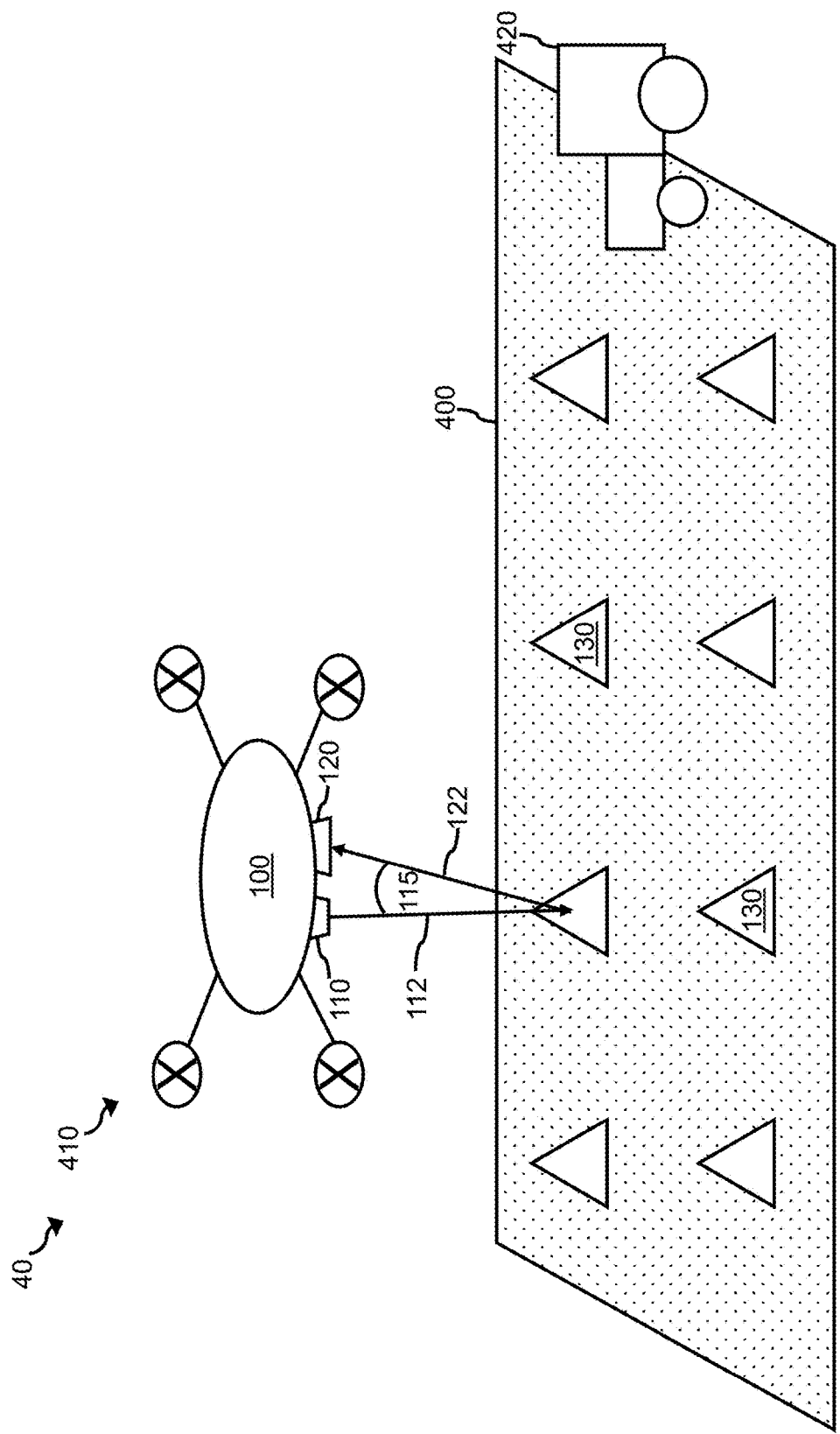
FIG. 4 is a block diagram of a quality condition detection system according to another embodiment.

FIG. 4 is a block diagram of a quality condition detection system 40 according to another embodiment. Quality condition detection system 40 can be the same as quality condition detection system 10 except that quality detection system 40 is configured to detect a quality condition of agricultural products 130 in vivo in a field 400 or agricultural setting. In quality condition detection system 40 the quality detection apparatus 100 is carried by a drone 410 or another aerial vehicle such as a plane, which can be autonomously- or manually-controlled. The quality detection apparatus 100 can wirelessly send an output signal to an automated vehicle 420 in the field 400 that can automatically harvest the desirable agricultural products 130 (e.g., that have a good quality condition).

Quality condition detection system 40 can use sunlight or moonlight to illuminate the agricultural products 130 in the field 400.

Figure 5:
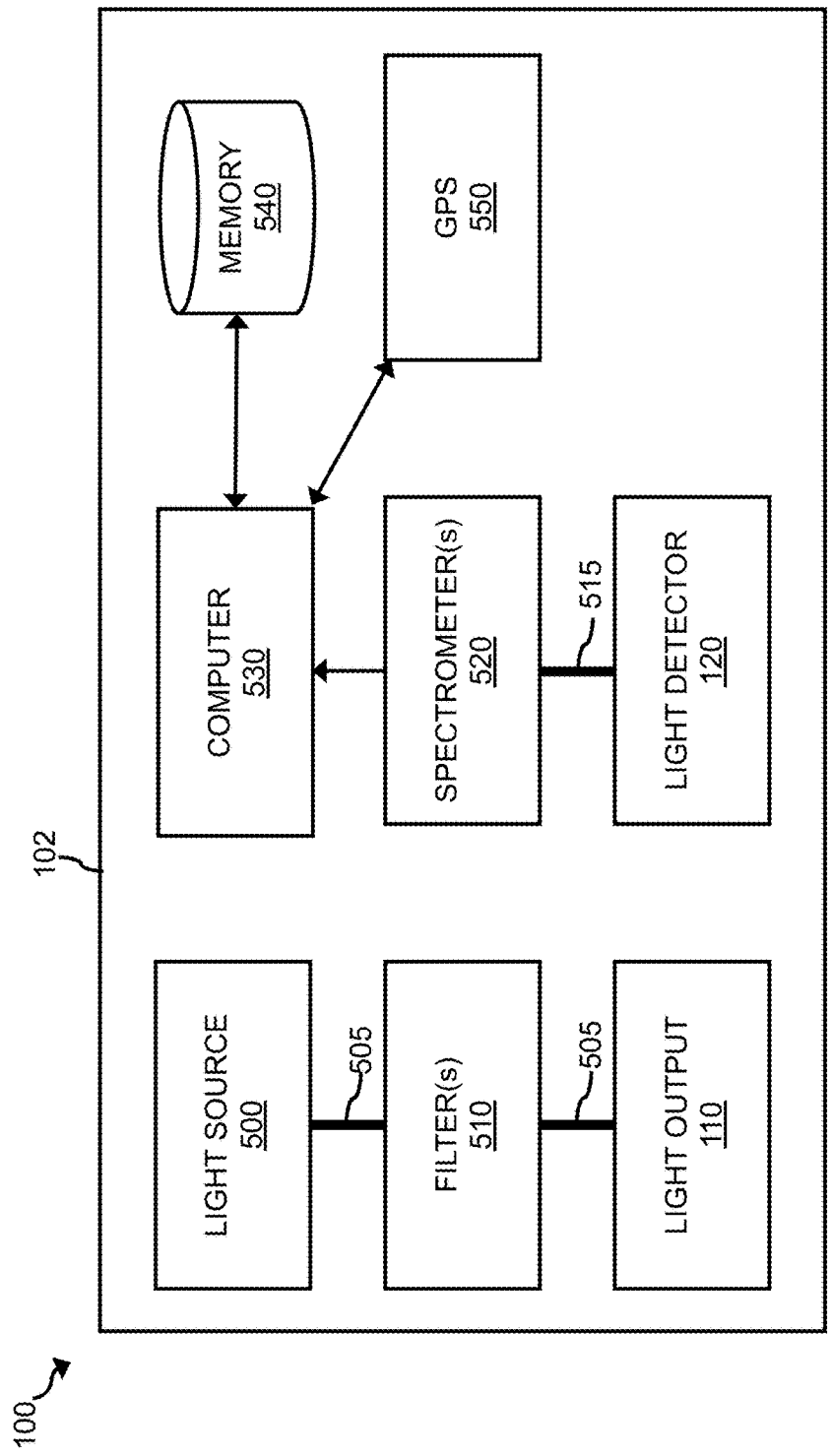
FIG. 5 is a block diagram of a quality detection apparatus according to an embodiment.

FIG. 5 is a block diagram of quality detection apparatus 100 according to an embodiment. Quality detection apparatus 100 includes a light source 500, an optional optical filter 510, light output 110, light detector 120, a spectrometer 520, and a computer 530. In some embodiments, light source 500 and light output 110 are optional, for example when the agricultural products are illuminated by sunlight, moonlight, or another light source.

Light 112 produced by the light source 500 is output from light output 110 where light 112 is directed towards an agricultural product 130, as discussed above. The light 112 can include at least some wavelengths to which the target agricultural product 130 is partially or highly optically transparent such that those wavelengths of light pass through at least a portion of the target agricultural product 130. The light 112 produced by the light source 500 can optionally pass through an optional optical fiber and/or light pipe 505 (in general, optical fiber 505) before the light 112 is output from light output 110.

In one example, the light source 500 includes one or more light-emitting diodes (LEDs). In another example, the light source 500 includes one or more supercontinuum light sources and/or lasers. In another example, the light source 500 includes a halogen light source such as a tungsten halogen light or a quartz halogen light. In one specific example, the tungsten halogen light source can be an HL-2000HP light source available from Ocean Optics, Inc.

In some embodiments, the light source 500 is optically coupled to one or more optional optical filter(s) 510 (e.g., a bandpass filter) to limit a broadband light source(s) to one or more predetermined spectral ranges (e.g., the UV, VIS, NIR-I, NIR-II, and/or SWIR part of the spectrum) such that the light exiting the optical filter 510 only consists of the predetermined spectral wavelength range(s). In a specific example, the optical filter(s) 510 can filter the light generated from light source 500 to a predetermined spectral wavelength range that is partially or highly optically transparent to the target agricultural product 500. In some embodiments, the light source 500 can emit pulsed light to allow for time-of-flight (TOF) measurements for the scattered, reflected, and/or diffracted signal, e.g., introducing measurement separation of charged molecules (ions). In some embodiments, the light output 110 is disposed on (and/or is integrated with) the light source 500, for example if the light source 500 includes one or more LEDs. In some embodiments, the light source 500 includes a combination of any of the foregoing. In some embodiments, the light 112 exiting the light output 110 can have a wavelength range of about 400 nm to about 2,500 nm, a wavelength range between about 400 nm and about 2,500 nm, or another wavelength range. Thus, the light 112 exiting the light output 110 can include a wavelength range of 400 nm to 700 nm, which corresponds to the visible part of the spectrum (VIS), a wavelength range of 700 nm to 1500 nm, which corresponds to the near infrared I (NIR I) part of the spectrum, a wavelength range of 1500 nm to 1900 nm, which corresponds to the near infrared II (NIR II) part of the spectrum, and/or a wavelength range of 1900 nm to 2500 nm, which corresponds to the short-wave infrared (SWIR) part of the spectrum. In addition or in the alternative, the spectral ranges can include the wavelength range of 200 nm to 400 nm, which corresponds to the near ultraviolet (UV) part of the spectrum.

As discussed above, the quality detection apparatus 100 can operate in a controlled lighting environment to avoid interference and noise from other light sources. In such a controlled lighting environment, the light detector 120 only collects light emitted from the light output 110, which is then reflected, refracted, deflected, and/or scattered by an agricultural product 130, as discussed above. The light 122 collected by the light detector 120 have a different wavelength range than the wavelength range of the light 112 exiting the light output 110. For example, the light 122 collected by the light detector 120 can have a wavelength range that is a subset of the wavelength range of the light 112 exiting the light output 110. In a specific example, the light 122 collected by the light detector 120 can have a wavelength range of about 400 nm to about 1,000 nm and the light 112 exiting the light output 110 can have a wavelength range of about 400 nm to about 2,500 nm.

The light output 110 and light detector 120 can be disposed on a common housing, such as the housing of a sensor head. The light output 110 and light detector 120 can be positioned at a predetermined distance from each other, which can be fixed using the common housing.

Disposing the light detector 120 on a common housing with the light output 110 can allow for repeatable operating conditions since the relative positions of and distance between the light output 110 and light detector 120 are fixed on the housing. In some embodiments, the light detector 120 can be adjustably disposed on the common housing such that the predetermined distance between the light output 110 and the light detector 120 can be adjusted as needed. Adjustably disposing the light detector 120 on a common housing can allow for different configurations within the same scan of the same target agricultural product 130 or between scans (e.g., between scans of the same or different agricultural products). In some embodiments, the light source 110 and the light detector 120 are disposed on repositionable platforms (e.g., via an actuator or other electromechanical mechanism), which can be adjusted by control signals generated by computer 530 or another microprocessor-based controller.

The light or light image 122 collected by the light detector 120 can be transmitted to one or more spectrometers 520 using optical fibers and/or optical fiber bundles 515 (in general, optical fibers 515). The optical fibers 515 can be transmissive in one or more predetermined spectral ranges (e.g., in the UV, VIS, NIR-I, and/or NIR-II part of the spectrum) and correspond to the wavelength range of the light 112 emitted from the light source 500, to the wavelength range of the light 112 that passes through the optional optical filter 510, and/or to the wavelength range of the light 122 collected by the light detector 120. In some embodiments, fore-optics are attached to the end of the light detector 120 to increase or decrease the numerical aperture of the light detector to optimize signal collection and, therefore, the signal-to-noise ratio. Alternatively, the optical fibers 515 can be omitted and the light detector 120 can transmit the collected light to the spectrometer(s) 520 using lenses, mirrors, and optical filters.

The spectrometer(s) 520 can include a diffractive optic comprising or consisting of planar, concave, and/or convex diffraction gratings, prisms, and/or optical elements that split the electromagnetic energy of the collected light into its respective wavelengths based on diffraction, refraction, absorption, and reflectance of the electromagnetic energy. This diffractive optic can be either a reflective diffractive optic or a transmission diffractive optic. This diffractive optic can comprise or consist of a series of parallel groove structures or it can be an aberration-corrected optic based on an optical profile of a non-parallel series of grooves. In addition to a scalar domain diffractive optic, one embodiment includes a resonance domain optical grating to provide very high efficiency and spectral resolution over a particular spectral bandpass dictated by the spectral signature of the condition under measurement. The spectrometer(s) 520 can have a concentric, reflective design operating in one or more of the spectral or wavelength ranges discussed above (e.g., in the UV, VIS, NIR-I, NIR-II, and/or SWIR region of the electromagnetic spectrum) or the spectrometer can have a transmissive design with prisms operating in one or more of the spectral or wavelength ranges discussed above. In some embodiments, the spectrometer(s) 520 can be the same as or similar to the spectrometers described in U.S. Pat. No. 6,266,140, titled "Corrected Concentric Spectrometer," which issued on Jul. 24, 2001, U.S. Pat. No. 7,518,722, titled "Multi-Channel, Multi-Spectrum Imaging Spectrometer," which issued on Apr. 14, 2009, and/or U.S. Pat. No. 6,839,136, titled "Holographic Grating Spectrum Analyzer," which issued on Jan. 4, 2005, which are hereby incorporated by reference. The spectrometer(s) 520 can also include a focal plane array detector or a linear array detector (e.g., to form a spectrograph), to record the optical signals created and the resulting spectroscopic scatter. The output(s) of the spectrometer(s) 520 is/are transmitted to a microprocessor-based signal and algorithm processing computer 530, which can analyze and/or transmit the data to another computer.

Figure 16:
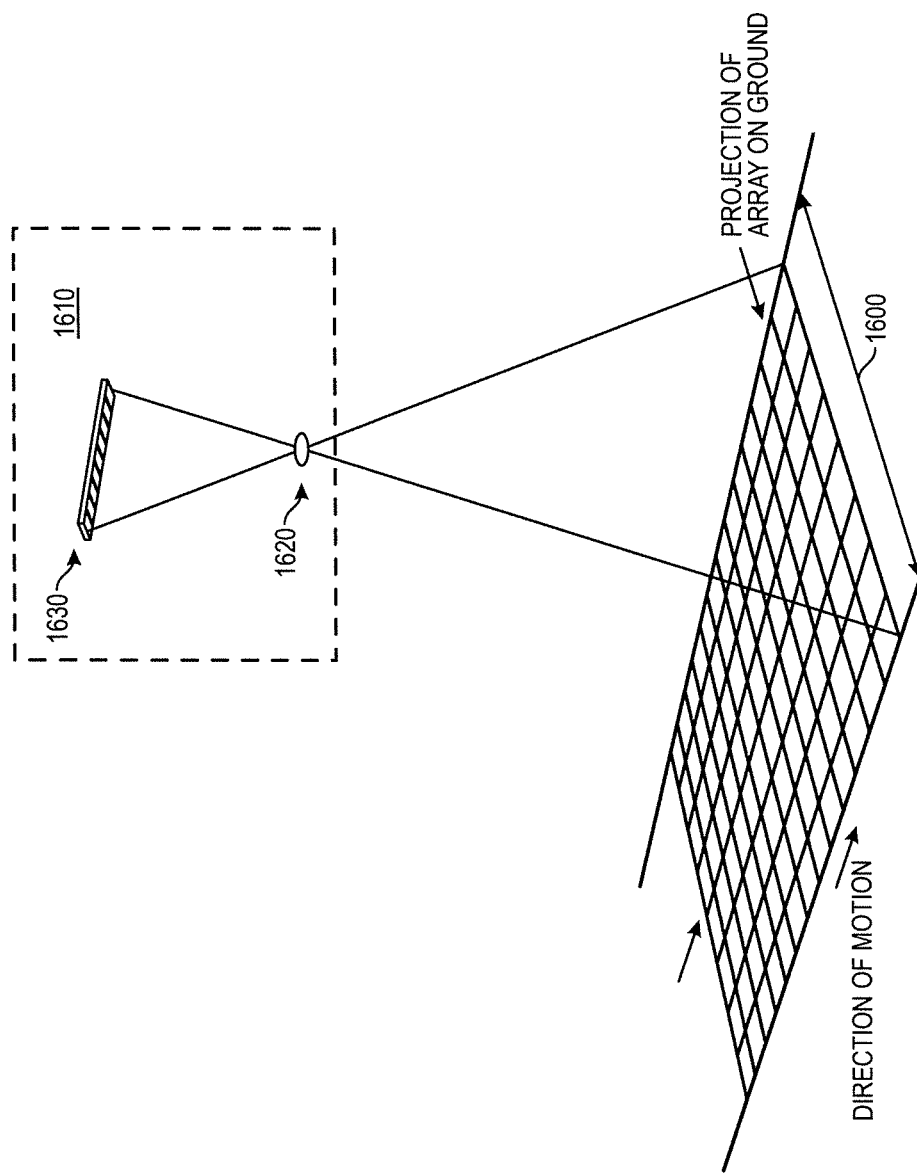
FIG. 16 illustrates an example of a field-of-view of an example spectrograph.

The spectrometer 520 (or spectrograph) has a field-of-view (FOV) that corresponds to the sample lateral area captured by a single image (or a single frame of a composite image). The fore-optics attached to the end of the light detector 120 can be designed to image the desired FOV onto the entrance slit plane of the spectrometer 520 with minimal optical distortion (aberration). An example of a FOV 1600 of an example spectrograph 1610 is illustrated in FIG. 16. The size of the FOV 1600 can be based on the focal length of the lens or fore-optics 1620 in the spectrograph 1610, the slit height (e.g., entrance slit 700 (below)), and/or the size of the focal plane array 1630.

The spectrometer 520 can also be designed to accommodate the variation in height of the agricultural products 130 in the sample area while maintaining focus (e.g., onto the focal plane array (FPA)). In other words, the spectrometer can have a depth of field (DOF) that accommodates the variation in height of the agricultural products 130 in the sample area.

The computer 530 can be operatively coupled to an optional storage device 540 that can include data relevant to the spectral scan. The computer 530 can be coupled to the storage device 540 via a wired connection or a wireless connection. In addition, the storage device 540 can be disposed locally or remotely from the computer 530. The storage device 540 can include non-transitory computer-readable memory.

The computer 530 can be programmed to perform one or more image pre-processing algorithms. The pre-processing algorithm(s) can be used to determine if a sufficient quantity of spectral scan data has been collected data and/or whether the spectral scan data is sufficiently clear. Sufficient quantity can include the collection of enough reflected, refracted, or scattered light from the sample area. Sufficient quantity can also include that the individual regions of the sample area are correctly represented in the spectral scan data. For example, speed variation or acceleration due to individual truck drivers may mean certain areas of the sample area are in view of the sensor for shorter or longer exposure times. Sufficient clarity in the spectral scan data can include the avoidance of interfering light, such as light reflected from metal surfaces of a truck or light scattered by foreign objects within the sample area. These factors can be controlled to some degree by image pre-processing.

The pre-processing algorithm(s) can identify and crop out portions of spectral scan data outside a boundary, or they may thin out portions of data to provide equalized contributions to the overall assessment. The pre-processing algorithm(s) can compare the spectral scan data with reference spectral scan data that has been manually pre-labeled to indicate which portions to include and/or to exclude to determine how/where to crop the spectral scan data. In some embodiments, the pre-processing algorithm(s) can identify occasions when the pre-processing algorithm(s) is faulty because the pre-processing cannot correct for these errors. In this case, the software would alert the user to re-scan the agricultural products.

The storage device 540 can include data from reference spectral scans of the agricultural product of interest having one or more quality conditions. For example, the storage device 540 can include data from reference spectral scans of the agricultural product in a healthy state and/or data from reference spectral scans of the agricultural product having one or more of the quality conditions described herein. The reference spectral scan can be taken of a reference agricultural product, which is the same type of agricultural product as the target agricultural product (e.g., both the target and reference agricultural products are oranges or the same variety or species of oranges). The data from the reference spectral scans can include the spectral signature of the agricultural product in a known state or condition (e.g., in a healthy state, a diseased state, infected with a pathogen, an overripe state, an under-ripe state, a contaminated state, etc.). The reference spectral scan data are preferably collected at the same spectral angle as the spectral angle 115 used to scan the agricultural products 130, as discussed above, so the spectral scan data are comparable In a specific example, the storage device 540 includes data from reference spectral scans of oranges (e.g., a specific variety or species of orange) having known Brix contents, which can span a range of about 0 to about 70, or another range. In certain applications, the range of interest is about 8 to about 14. A high Brix content (e.g., about 11 or above) can correspond to a riper and/or sweeter orange, which may be desirable for producing orange juice. A low Brix content (e.g., below about 11) can correspond to an under-ripened, bitter, and/or sour orange, which is less desirable for producing orange juice. The Brix content can be determined or confirmed through wet chemistry or another technique (e.g., after the reference scan is made).

Additionally or alternatively, the storage device 540 can include data from reference spectral scans of oranges (e.g., a specific variety or species of orange) having known limonin concentrations in the range of about 1 to about 5. A low limonin concentration (e.g., about 3 or below) can correspond to a riper and/or sweeter orange while a high limonin concentration (e.g., above about 3) can correspond to an under-ripened, diseased (e.g., with HLB disease, citrus greening disease, or another disease), bitter, and/or sour orange. The limonin concentration content can be determined or confirmed through wet chemistry or another technique (e.g., after the reference scan is made).

In another example, the storage device 540 includes data from reference spectral scans of citrus fruit (e.g., oranges such as a specific variety or species of orange) having HLB disease or citrus greening disease. The storage device 540 can also include data from reference spectral scans of citrus fruit (e.g., oranges such as a specific variety or species of orange) that is/are known to be healthy (i.e., they do not have HLB disease, citrus greening disease, or another disease).

In another example, the storage device 540 includes data from reference spectral scans of raw meat (e.g., beef such as a specific cut or variety of beef) having a pathogen such as *Salmonella*. The storage device 540 can also include data from reference spectral scans of raw meat (e.g., beef such as a specific cut or variety of beef) that is/are known to be pathogen-free.

The computer 530 can be programmed to compare the current spectral scan data of the agricultural products 130 with the reference spectral scan data to determine if the agricultural products 130 are healthy and/or have one or more of quality conditions. The computer 530 can be programmed to compare the current spectral scan data with data from the first agricultural product group (i.e., having a condition such as HLB disease) and/or the second agricultural product group (i.e., without having the condition such as HLB disease) to determine whether the agricultural product 130 has or appears to have the condition (e.g., HLB disease). The computer 530 can include program instructions to use statistical analysis, such as multivariate statistical analysis or mathematical regression analysis, and derived spectral algorithms to perform the foregoing comparison and analysis. In some embodiments, the computer 530 can be programmed to label the regions/pixels of the current spectral scan data where a pathogen or contaminant is located, which can be used for further quality processing or quality analysis, such as to determine the quantity of the pathogen or contaminant.

In another example, a model of the reference spectral scan data can include a characteristic spectral signature that may indicate that the agricultural product has one or more of the conditions described herein. The characteristic spectral signature can occur at one or more wavelengths of the spectral scan data. In some embodiments, the computer 530 is programmed with an algorithm or other analytical tools to determine if the current spectral scan data of the agricultural product 130 has such a characteristic spectral signature. An example of a spectral signature is one or more relative intensity peaks or valleys at a corresponding one or more wavelengths.

In some embodiments, the computer 530 can be programmed to determine if the current spectral scan data of the agricultural product 130 includes a characteristic spectral signature without comparing the current spectral scan data to reference spectral data. For example, the computer 530 can be programmed to determine whether the measured spectral intensity (or relative intensity) levels of the target agricultural product 130 at certain wavelengths correspond to a spectral signature of the agricultural product. The computer 530 can be programmed to compare the current spectral scan data with data from the first or second agricultural product groups, as discussed above, to determine whether such a characteristic spectral signature is present. In other embodiments, the computer 530 can be programmed with an algorithm to determine if a characteristic spectral signature is present without comparing the current spectral scan data to reference spectral scan data (i.e., based solely on the absolute or relative spectral intensities and corresponding wavelengths of the current spectral scan data in the spectral signature).

In another aspect, the computer 530 can be programmed to output a graph or other visual representation (in general, graph) of the current spectral scan data, which can be transmitted over a network connection (e.g., a wireless network) to a user's computer (e.g., to a customer's computer, a technician's computer, or another computer), which can be a handheld computer (e.g., a smartphone), a mobile computer (e.g., a laptop), or a desktop computer, or a display in electrical communication with the computer 530. The computer 530 can be programmed to output a graph of reference spectral data from the same type or variety of agricultural product, which can be overlaid on the same graph as the current spectral scan data. In addition or in the alternative, the computer 530 can be programmed to output a graph of spectral data from a first agricultural product or product variety (e.g., having a first quality condition such as a first Brix content) and/or a second agricultural product or product variety (e.g., having a second quality condition such as a first limonin content), either or both of which can be overlaid on the same graph as the current spectral data.

In some embodiments, the computer 530 can be programmed to visually indicate where the spectral data are different to assist the viewer in visually comparing the spectral data. In addition, the computer 530 can include program instructions to output an alarm or other signal if it determines that the current spectral scan data is indicative of a poor quality condition (e.g., according to statistical analysis and/or a spectral signature, as described above). The alarm or signal can alert an assembly line worker to remove or further inspect the agricultural product with the detected poor quality condition. In addition or in the alternative, the alarm or signal can cause a machine (e.g., product sorter 310) to remove the agricultural product with the detected poor quality condition from the assembly line. In addition or in the alternative, the alarm or signal can cause gate 170 to open or shut to direct the truck 140 to the appropriate destination (e.g., to discard agricultural product having a poor quality condition or to a factory to process agricultural product having a good quality condition).

In addition or in the alternative, the computer 530 can be programmed to produce a first output signal if it determines that the current spectral scan data is indicative of a first quality grade (e.g., a poor quality grade), a second output signal if it determines that the current spectral scan data is indicative of a second quality grade (e.g., a low quality grade), a third output signal if it determines that the current spectral scan data is indicative of a third quality grade (e.g., a better quality grade), and/or a fourth output signal if it determines that the current spectral scan data is indicative of a fourth quality grade (e.g., a best quality grade). The first, second, third, and fourth output signals can be visual and/or audible (e.g., an alarm or other sound) that can be distinctive for each output and corresponding quality grade. The output signal can alert an assembly line worker to remove or further inspect the agricultural product based on the detected quality condition(s). In addition or in the alternative, the alarm or signal can cause a machine (e.g., product sorter 310) to remove the agricultural product lower-quality conditions (e.g., poor and/or low quality grades) from the assembly line and/or to sort the agricultural product according to the detected quality condition. In addition or in the alternative, the alarm or signal can cause gate 170 to open or shut to direct the truck 140 to the appropriate destination (e.g., to discard agricultural product having poor and/or low quality grades or to a factory to process agricultural product having better and/or best quality grades). The quality grades can be based on and/or can correspond to the Brix and/or limonin content measured by the quality detection apparatus.

For example, when the agricultural product is an orange (e.g., a navel orange), the first output signal can be produced when the measured Brix content is between 0 and a first threshold Brix content (e.g., 9) and/or when the measured limonin content is between a first threshold limonin content (e.g., 5) and a second limonin content (e.g., 4). The second output signal can be produced when the measured Brix content is between the first threshold Brix content (e.g., 9) and a second threshold Brix content (e.g., 11) and/or when the measured limonin content is between the second threshold limonin content (e.g., 4) and a third limonin content (e.g., 3). The third output signal can be produced when the measured Brix content is between the second threshold Brix content (e.g., 11) and a third threshold Brix content (e.g., 12) and/or when the measured limonin content is between the third threshold limonin content (e.g., 3) and a fourth limonin content (e.g., 2). The fourth output signal can be produced when the measured Brix content is between the third threshold Brix content (e.g., 12) and a fourth threshold Brix content (e.g., 14) and/or when the measured limonin content is between the fourth threshold limonin content (e.g., 2) and a fifth limonin content (e.g., 1).

When the quality detection apparatus 100 is disposed in a vehicle, such as a drone 410 or another aerial vehicle, the optional GPS 550 can be used to determine the geographic location (e.g., GPS coordinates) where each scan takes place to identify the geographic location of each scanned agricultural product 130. In one example, the geographic location of the scanned agricultural product 130 is sent to the automated vehicle 420 to harvest (or not harvest) the agricultural products 130 based on their quality condition(s). Additionally or alternatively, the quality detection apparatus 100 can determine its position through trilateration or triangulation of wireless signals.

Figure 6:
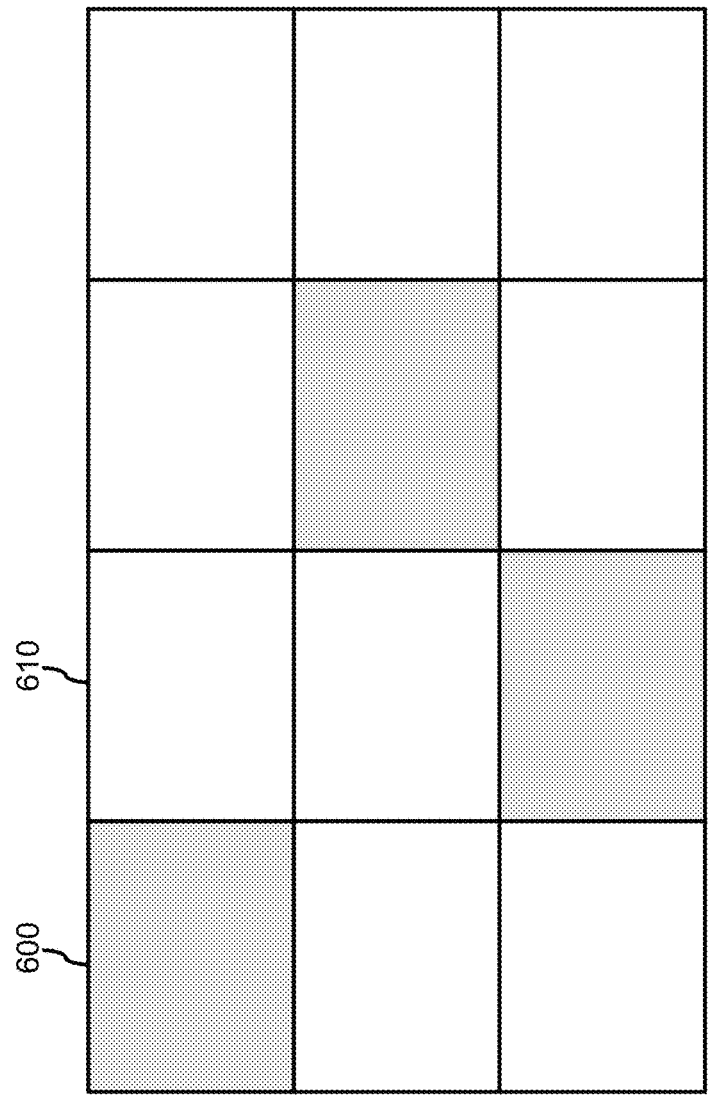
FIG. 6 is a block diagram of an example map of a quality condition of agricultural products in a field according to an embodiment.

FIG. 6 is a block diagram of an example map 60 of a quality condition of agricultural products 130 in a field. The map 60 includes geographic regions 600 where a condition is detected and geographic regions 610 where the condition is not detected. The map 60 can be generated by the computer 530 or it can generated by a second computer after the spectral and GPS data are transferred thereto.

Figure 7A:
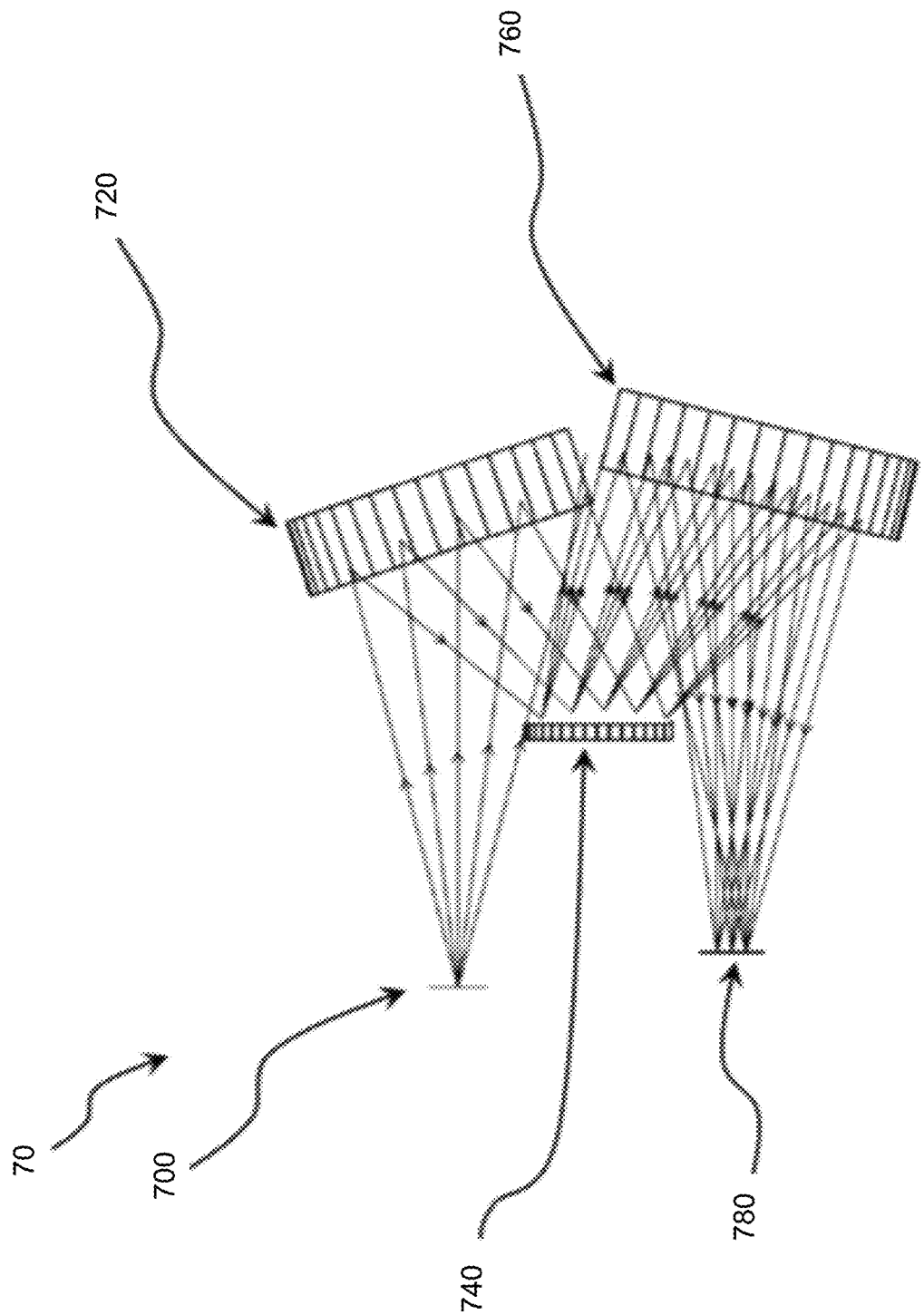
FIG. 7A illustrates an example of a spectrometer according to an embodiment.

FIG. 7A illustrates an example of a concentric, reflective spectrometer 70, which can be the same as spectrometer 520, according to an embodiment. The spectrometer 70 includes an entrance slit 700, a concave, concentric collimating mirror 720, a concentric, convex diffraction grating 740, a concentric, concave focusing mirror 760 and an electronic array imaging sensor 780. The spectrometer 70 is configured and arranged to operate in one or more of the spectral ranges described above (e.g., in the UV, VIS, NIR-I, NIR-II, and/or SWIR part of the spectrum) and corresponding to the wavelengths of light emitted from the light source 110. The imaging sensor 780 can be electrically coupled to a computer (e.g., to computer 530 in FIG. 5) to analyze and/or display the spectral content output of spectrometer 70. In some embodiments, the imaging sensor 780 is temporally gated to allow for time-of-flight (TOF) measurements. The spectrometer 70 can include a range of imaging sensors 780 based on materials comprised of either silicon, InGaAs (Indium-Gallium-Arsenide), or MCT/HgCdTe (mercury cadmium telluride) as determined by the spectral bandpass where the spectral signature(s) of the conditions is/are evident. The spectrometer 70 can be included in any of the embodiments described herein, such as in quality detection apparatus 100.

An alternative embodiment includes a transmissive spectrometer(s), which may include a prism-grating-prism design operating in one or more the spectral ranges described above (e.g., in the UV, VIS, NIR-I, NIR-II, and/or SWIR part of the spectrum). Another embodiment of a spectrometer(s) includes a concentric catadioptric design operating in one or more the spectral ranges described above (e.g., in the UV, VIS, NIR-I, NIR-II, and/or SWIR part of the spectrum). The imaging sensor (e.g., imaging sensor 780) in any of these embodiments can be temporally gated to allow for TOF measurements.

Figure 7B:
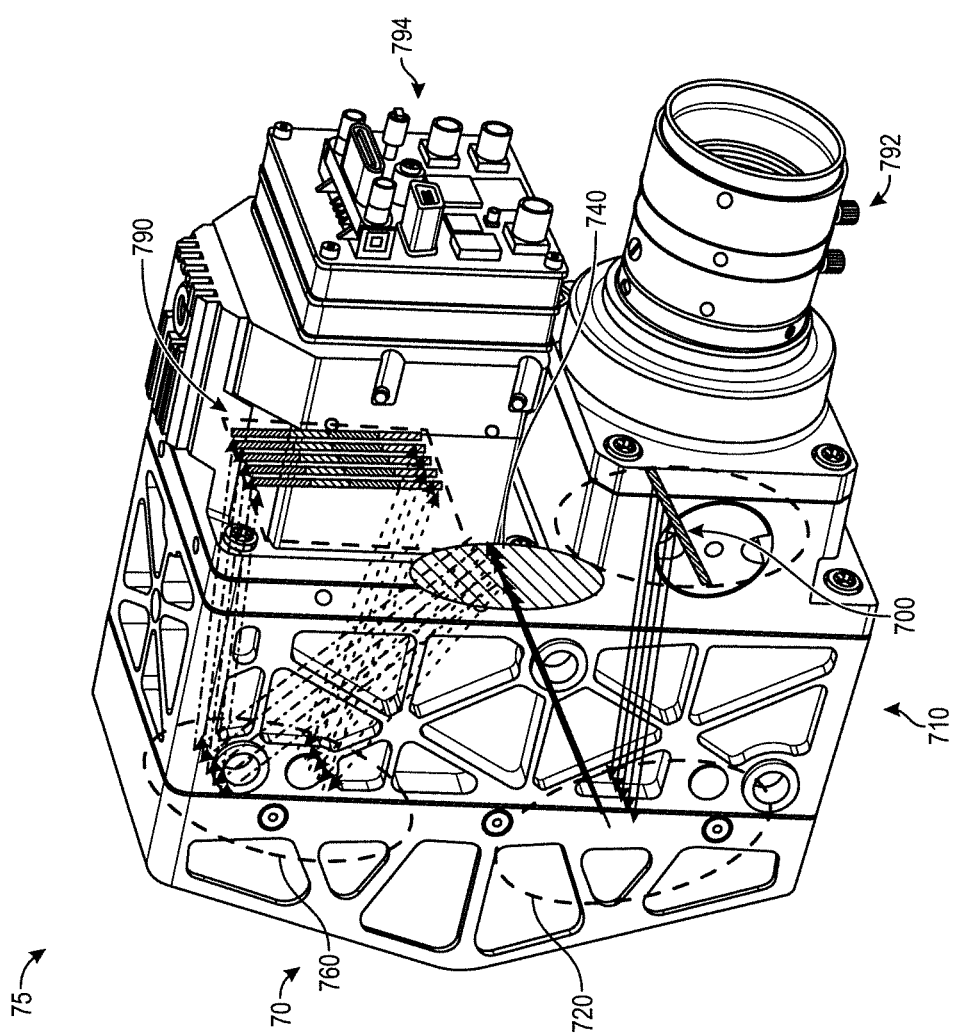
FIG. 7B illustrates an example of a spectrograph according to an embodiment.

FIG. 7B illustrates an example of a spectrograph 75 according to an embodiment. The spectrograph 75 includes the spectrometer 70, a focal plane array detector 790, a lens 792 or other fore-optics, and a controller 794, which are located in a housing 710. The spectrometer 70 has an input that is optically coupled to the lens 792 and an output that is optically coupled to the focal plane array detector 790, which is configured to detect the light spectrum produced by the spectrometer 70. The controller 794 is electrically coupled to the focal plane array detector 790. The controller 794 includes memory that stores firmware and/or software as described herein.

Figure 8:
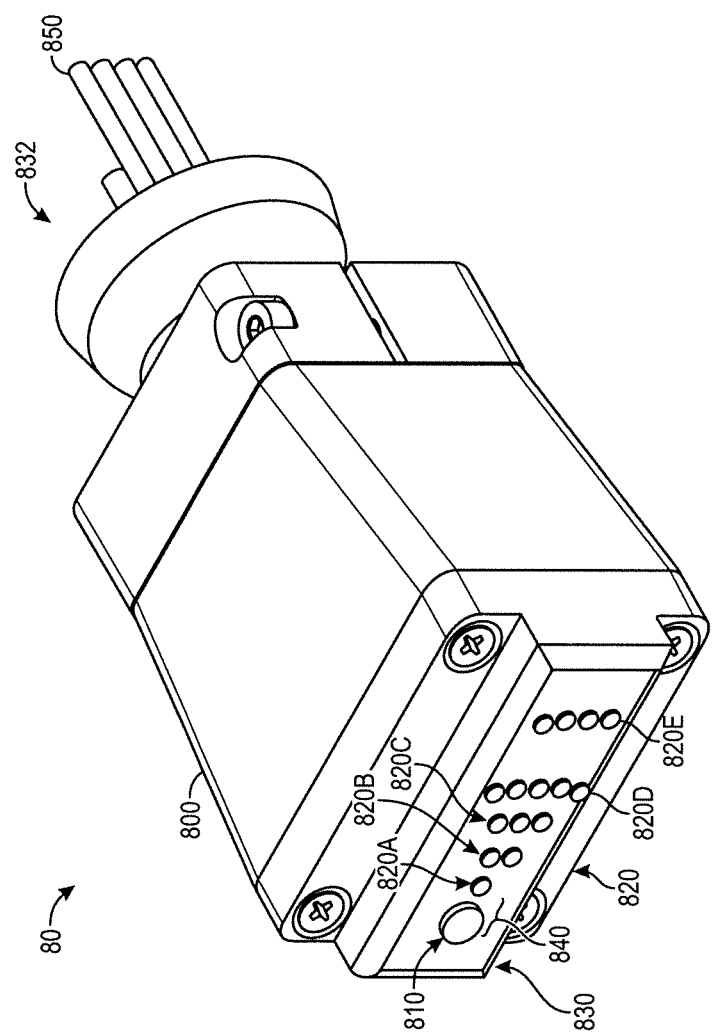
FIG. 8 illustrates a sensor head according to an embodiment.

FIG. 8 illustrates a sensor head 80 according to one or more embodiments. The quality detection apparatus 100 can include one or more sensor heads 80 in some embodiments. Sensor head 80 includes a housing 800, a light output 810, an array of light detectors 820, and optical fibers and/or light pipes (collectively, optical fibers 850). In some embodiments, the light output 810, light detectors 820, and optical fibers 850 can be the same as light output 110, light detector 120, and optical fibers 505, 515, respectively. The light output 810 and light detectors 820 are mounted on a proximal end 830 of the housing 800. Thus, the housing 800 can set the spatial geometry and orientation between the light output 810 and the light detectors 820. The light detectors 820 can include lenses, mirrors, and optical filters to collect and condition the received light.

The optical fibers 850 extend from a distal end 832 of the housing 800. The optical fibers 850 can extend to (e.g., can be optically coupled to) the light detectors 820 and/or to the light output 810.

The light output 810 can be optically coupled to one or more optical fibers 850 to receive light from a light source, such as light source 500 (FIG. 5). In addition or in the alternative, the light output 810 can include a light source (e.g., an LED or a laser) and/or a light source can be disposed in the housing 800, in which case the light source is optically coupled to the light output 810 (e.g., with or without one or more optical fibers). In some embodiments, a lens, a collimator, or other optics can be disposed on the light output 810 or between the light output 810 and the light source to alter the optical properties of the light that exits the light output 810. In addition or in the alternative, an optical filter can be disposed between the light output 810 and the light source.

The light detectors 820 are disposed at fixed radial distances and angular positions from the light output 810 and from other light detectors 820. As illustrated, the number of light detectors 820 varies with the radial distance from light output 810. For example, one light detector 820A is located closest to light output 810 at a first radial distance 840 (e.g., 5 mm) or a first group predetermined radial distance from light output 810, followed by a group 820B of two light detectors 820 located at a second radial distance (e.g., 10 mm) or a second group predetermined radial distance from light output 810, a group 820C of three light detectors 820 located at a third radial distance (e.g., 15 mm) or a third group predetermined radial distance from light output 810, a group 820D of five light detectors 820 located at a fourth radial distance (e.g., 20 mm) or a fourth group predetermined radial distance from light output 810, and a group 820E of four light detectors 820 located at a fifth radial distance (e.g., 30 mm) or a fifth group predetermined radial distance from light output 810. Thus, the number of light detectors 820 in each group 820A-E is not uniform in this embodiment.

In other embodiments, each group 820A-E can have the same number of light detectors 820. In yet other embodiments, each group 820A-E can have a different number of light detectors 820, though not necessarily following the number of light detectors 820 per group 820A-E illustrated in FIG. 8. In addition, other embodiments can include additional or fewer groups 820A-E of light detectors 820. Each group 820A-E of light detectors 820 can be spaced at regular or irregular distances from the light output 810. Additionally, the light detectors 820 within a given group can be spaced at regular or irregular distances from one another and/or regular or irregular angular positions with respect to light output 810. In some embodiments, only a single light detector 820 is disposed on the sensor head 800. In some embodiments, the light detectors 820 are spaced within a range of 0 to 5 centimeters from the light output 810, which can optimize the sampled depths.

In some embodiments, the sensor head 80 can have more than one light output 810, and each light output 810 can be optically coupled to the same or to a different light source. The light outputs 810 can be grouped or clustered together or they can be disposed in different positions on the proximal end 830 of the housing 800. In one example, the light outputs 810 are grouped in virtual columns or virtual arcs, similar to the "vertical" light detector groups 820A-E illustrated in FIG. 8. In another example, the illumination outputs 810 are disposed laterally along some or all of the length of the proximal end 830 of the housing 800.

The optical fibers 850 can optically couple the light detectors 820 to one or more spectrometers 520 (e.g., as illustrated in FIG. 5) to deliver the collected light thereto. In some embodiments, each light detectors 820 is optically coupled to its own spectrometer. Alternatively, two or more light detectors 820 can be optically coupled to the same spectrometer. For example, the light detectors (s) 820 in each light detector group 820A-E can be connected to a common spectrometer. In some embodiments, fore optics are attached to the end of the optical fibers 850 (e.g., proximal to the respective light detector 820) to increase or decrease the numerical aperture of the light detectors 820.

It is noted that FIG. 8 illustrates an example embodiment and one skilled in the art will appreciate that the number of light outputs 810, the number of light detectors 820, the number of optical fibers 850, and/or their respective configuration and arrangement can vary. FIG. 8 illustrates an example of one physical pattern and arrangement of the foregoing.

In some embodiments, multiple sensor heads 80 can be included in the quality detection apparatus 100. For example, multiple sensor heads 80 can be disposed above the truck 140, above the conveyor belt 300, and/or in the drone 410. Each sensor head 80 can the same, substantially the same, or different than the others. In some embodiments, one or more of the multiple sensor heads 80 is/are configured to detect for a first quality condition in the agricultural product 130 using a first predetermined wavelength range of light energy and one or more of the multiple sensor heads 80 is configured to detect for a second quality condition in the agricultural product 130 using a second predetermined wavelength range of light energy. The first and second predetermined wavelength ranges can be the same as or different than each other, or they can partially or fully overlap each other.

Figure 9:
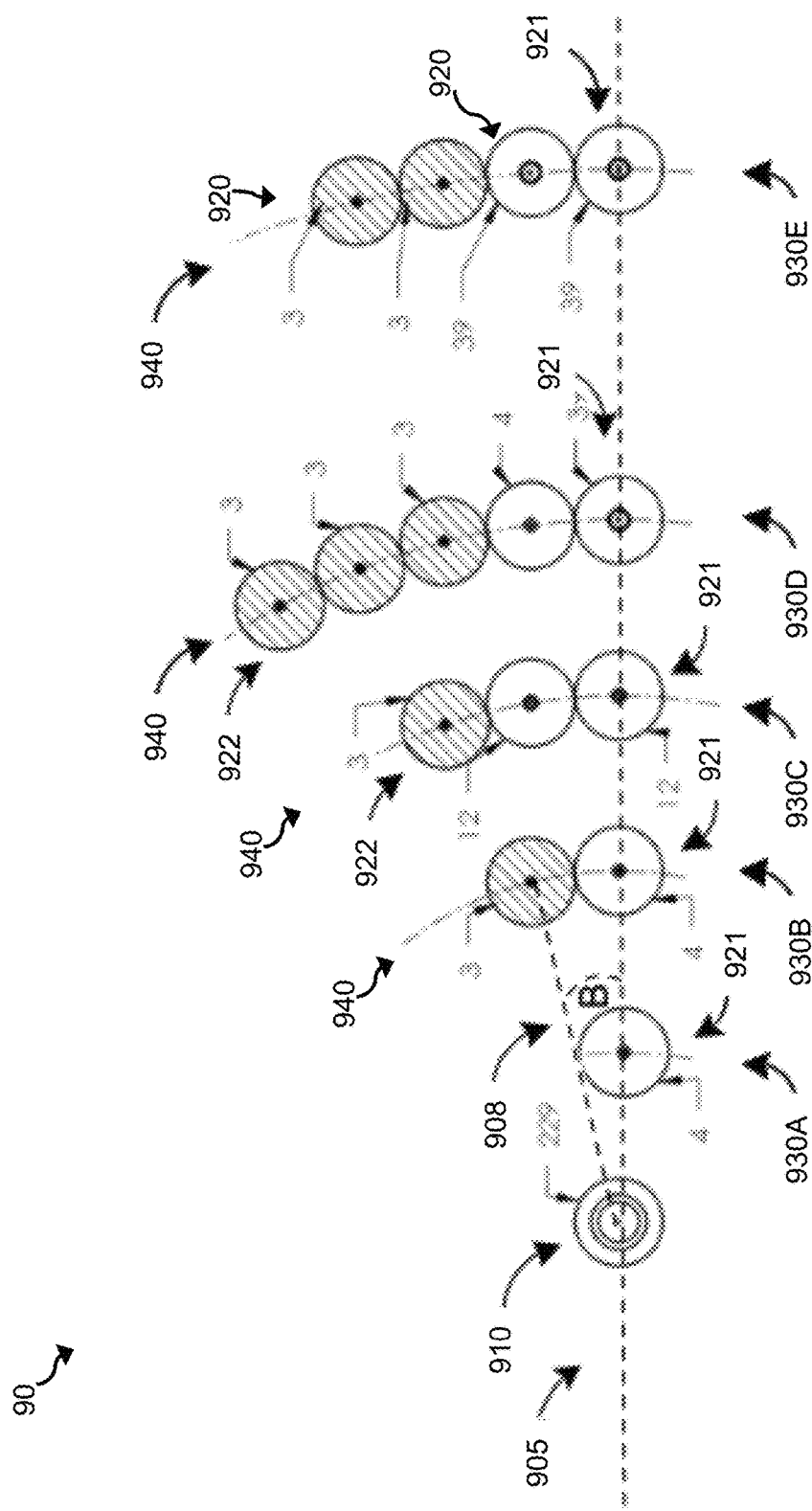
FIG. 9 illustrates an alternative embodiment of the configuration, arrangement, and geometry of a light output and light detectors.

FIG. 9 illustrates an alternative embodiment of the configuration, arrangement, and geometry 90 of a light output 910 and light detectors 920, which can be the same as or different than the light output 810 and light detectors 820, respectively. For example, in some embodiments, the light output 810 and light detectors 820 on sensor head 80 can be configured and arranged in the manner illustrated in FIG. 9. In FIG. 9, a reference axis 905 extends through the light output 910, the first light detector 921 of each light detector group 930A-E, such as through the center of the light output 910 and through the center of each first light detector 921. The angular position of each light detector 920 can be defined with respect to reference axis 905. For example, the first light detector 921 of each light detector group 930A-E has an angular position of 0 or 360 degrees. In another example, the angular position of the second light detector 920 in light detector group 930B is defined by a line 908 that passes through the center of the light output 910 and through the center of the second light detector 920 in light detector group 930B. The angle between line 908 and reference line 905 is angle B, which is the angular position of the second light detector 920 in light detector group 930B. The angular positions of the other light detectors 920 are determined in the same way.

The light detectors 920 in each light detector group 930A-E are disposed adjacent to each other along a virtual arc 940. The virtual arc 940 for a given light detector group 930A-E has a virtual radius from light output 910 equal to the radial distance of the light detector 920 from light output 910 in the respective light detector group 930A-E. For example, the radial distance of the light detectors 920 in light detector group 930C is equal to the virtual radius of the virtual arc 940 on which the light detectors 920 in light detector group 930C are disposed. The radial distance and virtual arc 940 radius of the light detector 920 in group 930A can be about 5 mm. The radial distance and virtual arc 940 radius of the light detectors 920 in group 930B can be about 10 mm. The radial distance and virtual arc 940 radius of the light detectors 920 in group 930C can be about 15 mm. The radial distance and virtual arc 940 radius of the light detectors 920 in group 930D can be about 20 mm. The radial distance and virtual arc 940 radius of the light detectors 920 in group 930E can be about 30 mm.

In the embodiment in which the light detectors 920 comprise the polished ends of one or more fiber optic bundles, FIG. 9 illustrates an example of the number of optical fiber bundles that can be optically coupled to and/or that comprise the light output 910 and light detectors 920. Each optical fiber bundle includes one or more (e.g., a plurality of) optical fibers. Each optical fiber can have a 50-micron diameter or another diameter. Specifically, FIG. 9 indicates that the light output 910 includes 229 optical fiber bundles. The light detector 920 in light detector group 930A includes 4 optical fiber bundles. The first light detector 921 in light detector group 930B includes 4 optical fiber bundles; the second light detector 920 in light detector group 930B includes 3 optical fiber bundles. The first light detector 921 in light detector group 930C includes 12 optical fiber bundles. The other light detectors 920 in light detector group 930C include 12 and 3 optical fiber bundles, respectively, in the upward direction in FIG. 9 (i.e., away from the first light detector 921 in light detector group 930C). The first light detector 921 in light detector group 930D includes 39 optical fiber bundles. The other light detectors 920 in light detector group 930D include 4, 3, 3, and 3 optical fiber bundles, respectively, in the upward direction in FIG. 9 (i.e., away from the first light detector 921 in light detector group 930D). The first light detector 921 in light detector group 930E includes 39 optical fiber bundles. The other light detectors 920 in light detector group 930E include 39, 3, and 3 optical fiber bundles, respectively, in the upward direction in FIG. 9 (i.e., away from the first light detector 921 in light detector group 930E). Thus, the number of optical fibers or optical fiber bundles coupled to each light detector 920 in a given light detector group 930A-E can correspond to the angular position of the light detector on the corresponding virtual arc of the light detector group 930A-E. In addition, the number of optical fibers or optical fiber bundles coupled to each light detector 920 can vary as a function of the radial distance of the light detector group. Those skilled in the art will appreciate that the number, configuration, and/or arrangement of light detectors 920, light detector groups 930A-E, and fiber optic bundles (e.g., the number of fiber optic bundles that are optically coupled to each light detector 920) illustrated in FIG. 9 is provided as a non-limiting example, and that other configurations and/or arrangements are possible.

In some embodiments, the hashed light detectors 922 indicate optional light detectors 920. A non-functioning spacer light detector can be disposed in the location of each hashed light detector 922 when the hashed light detectors 922 do not comprise functional light detectors 920. In some embodiments, one or more hashed light detectors 922 can be a non-functioning spacer light detector(s) and one or more light detectors 922 can be a functioning light detector(s) 920. In some embodiments, spacer light detectors are provided to reduce and/or limit crosstalk between adjacent light detector groups.

Figure 10:
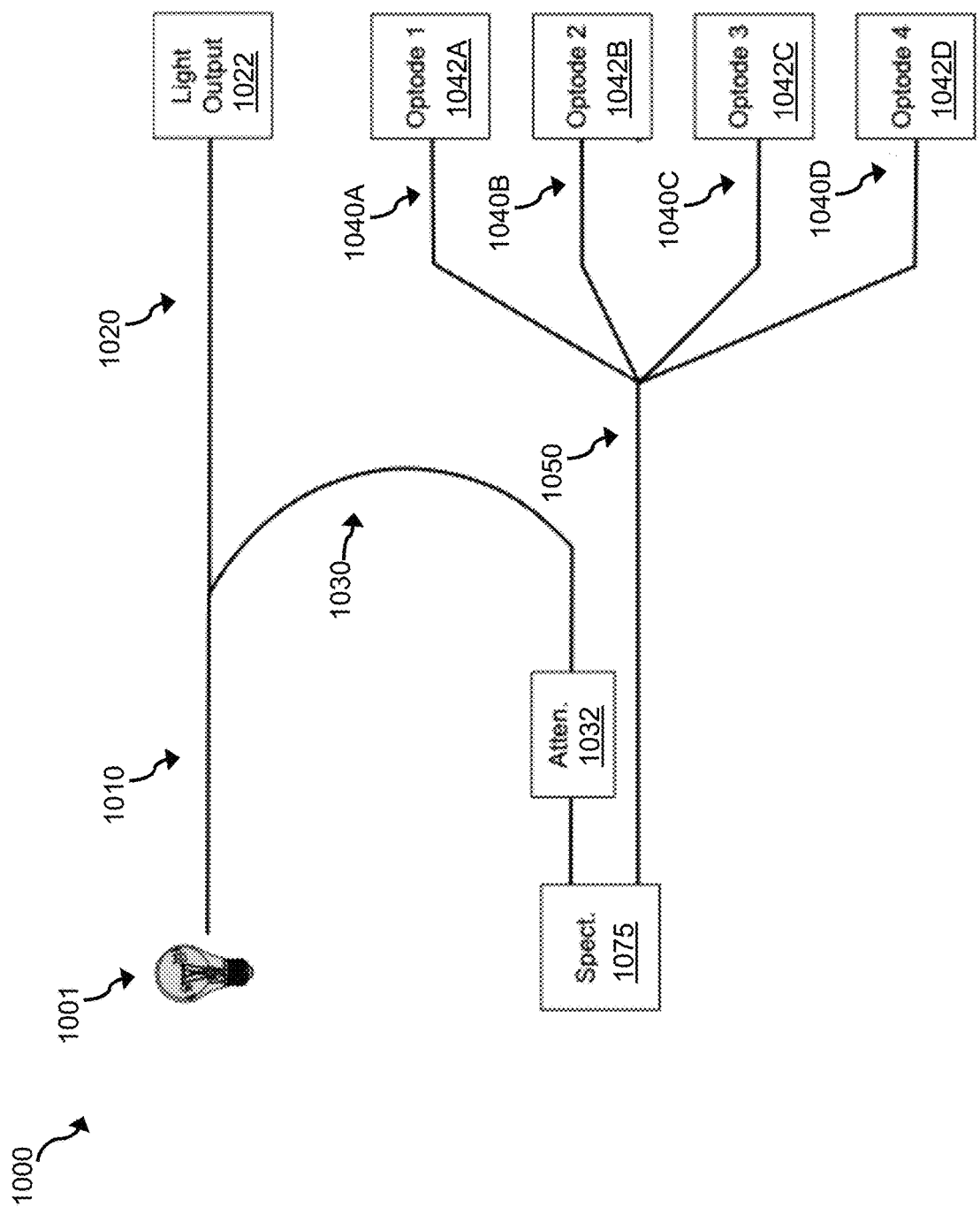
FIG. 10 is a simplified diagram of a fiber optic probe according to an embodiment.

FIG. 10 is a simplified diagram of a fiber optic probe 1000 according to one or more embodiments. The probe 1000 optically couples (a) the light or illumination source to the light output and (b) the light detectors to the spectrometer(s). The probe 1000 can be disposed in the housing (e.g., in housing 800) of the sensor head and/or in housing 102. A first fiber bundle 1010 is optically coupled to light source 1001. Light source 1001 can be the same as or similar to light source 500. The first fiber bundle 1010 includes a plurality of optical fibers, such as 232 optical fibers (e.g., 50-micron optical fibers) in some embodiments. The first fiber bundle 1010 is optically coupled to second and third fiber bundles 1020, 1030. The second fiber bundle 1020 is optically coupled to the first fiber bundle 1010 and to light output 1022, which can be the same as light output 110, 810, and/or 910. The second fiber bundle 1020 includes a plurality of optical fibers, such as 229 optical fibers (e.g., 50-micron optical fibers) in some embodiments. The third fiber bundle 1030 is optically coupled to the first fiber bundle 1010, to an optical attenuator 1032, and to spectrometer(s) 1075. The third fiber bundle 1030 includes a plurality of optical fibers, such as 3 optical fibers (e.g., 50-micron optical fibers) in some embodiments. The optical attenuator 1032 can attenuate the intensity of a portion of the light emitted from light source 1001 for use as a reference light/signal in the spectrometer(s) 1075. In some embodiments, the optical attenuator 1032 attenuates the light by a factor of about 1,000,000 (i.e., 1,000,000:1).

Each light detector or light detector group 1042A-D is optically coupled to or comprises a respective fourth fiber bundle 1040A-D, similar to the embodiments described herein. For example, each light detector or light detector group 1042A-D can comprise the polished tips of the optical fibers in the respective fourth fiber bundle 1040A-D. The fourth fiber bundles 1040A-D are optically coupled to a fifth fiber bundle 1050, which is coupled to the spectrometer(s) 1075. In an alternative embodiment, each fourth fiber bundle 1040A-D is directly coupled to the spectrometer(s) 1075. In some embodiments, each fourth fiber bundle 1040A-D is directly coupled to a corresponding spectrometer 1075 such that each fourth fiber bundle 1040A-D and each light detector or light detector group 1042A-D has a dedicated spectrometer 1075. Each fourth fiber bundle 1040A-D includes one or a plurality of optical fibers (e.g., 50-micron optical fibers) and/or one or a plurality of optical fiber bundles (e.g., as discussed above). In some embodiments, each fourth fiber bundle 1040A-D includes 3-39 optical fibers (e.g., 3, 4, 12, and/or 39 optical fibers) or 3-39 optical fiber bundles. In some embodiments, at least one of the fourth fiber bundles 1040A-D is optically coupled to an inactive light detector or light detector group (e.g., a spacer), such as fiber bundle 1040A and light detector or light detector group 1042 in some embodiments. The fourth fiber bundles 1040A-D can include additional or fewer optical fiber bundles which can be optically coupled to a corresponding additional or fewer light detectors. In some embodiments, the fourth fiber bundles 1040A-D includes up to 14 fiber bundles (i.e., bundles 1040A-M (not illustrated)) that are optically coupled to up to 14 light detectors or light detector groups (i.e., light detectors or light detector groups 1042A-M (not illustrated)). As discussed above, some of the fiber bundles can be optically coupled to inactive or spacer light detectors or light detector groups.

Figure 11:
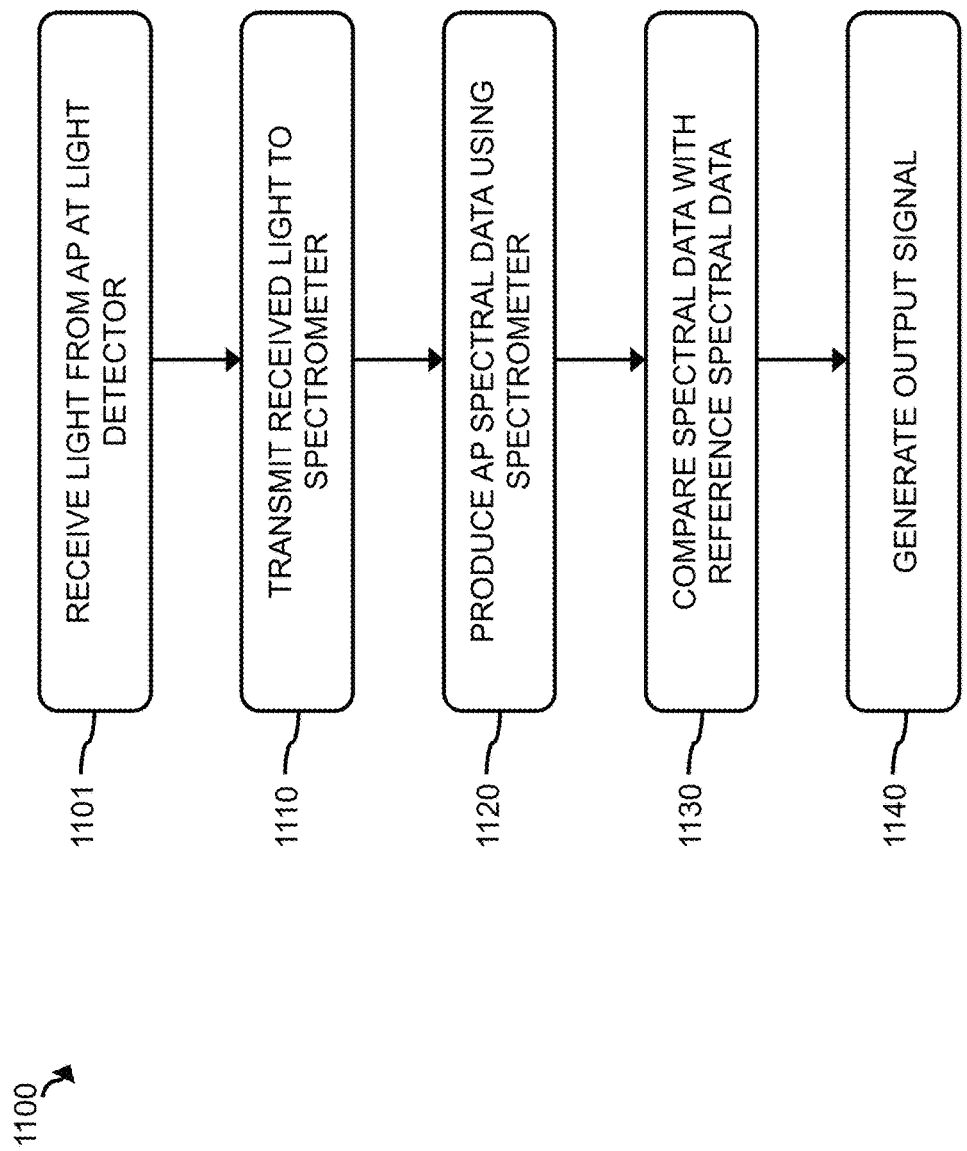
FIG. 11 is a flow chart of a method for determining a quality condition of an agricultural product according to an embodiment.

FIG. 11 is a flow chart of a method 1100 for determining a quality condition of an agricultural product according to an embodiment. Method 1100 can be performed with any of the apparatus and systems described herein. In step 1101, a light is received at a light detector. The received light includes scattered, refracted, and/or reflected light from an agricultural product.

Figure 17:
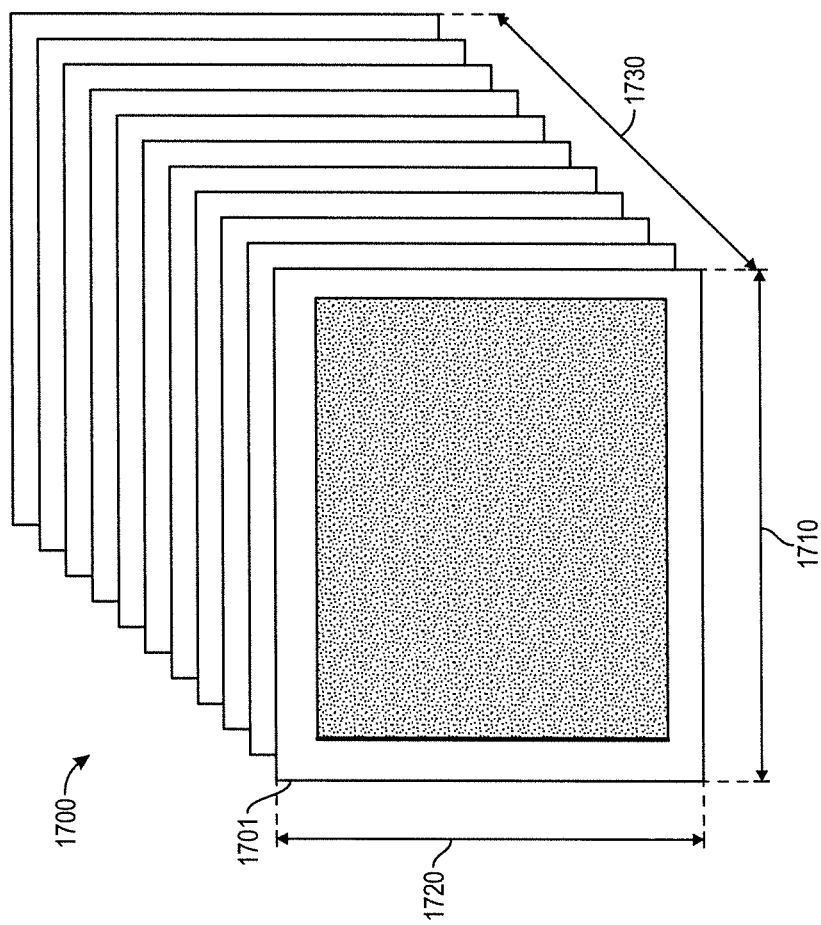
FIG. 17 illustrates an example of spectral scan data according to an embodiment.

In step 1110, the received light is transmitted to a spectrometer, which can be the same as spectrometer 520, 70. In step 1120, the spectrometer produces agricultural product (AP) spectral scan data of the received light. The AP spectral data can include the measured intensity of the light at each of a plurality of wavelengths. An example of spectral scan data 1700 is illustrated in FIG. 17. The spectral scan data 1700 includes a plurality of frames 1701 that represent spectral scan data across the FOV of the spectrometer, which can correspond to the width (e.g., in the spatial "X" direction 1710) and depth (e.g., in the spatial "Z" direction) of the sample area. Each frame 1701 represents a different spatial position along the length of the sample area (e.g., in the spatial "Y" direction 1730).

In step 1130, the AP spectral data is sent to a computer that is in electrical communication with the spectrometer. The computer compares the AP spectral data with reference spectral data of the agricultural product. The reference spectral data can correspond to agricultural products having known quality conditions. The reference spectral data is for the same type, variety, and/or species of agricultural product as the agricultural product from which the light is received in step 1101. For example, when the agricultural product from which the light is received in step 1101 is a navel orange, the reference spectral data is also for navel oranges having known quality conditions, such as known Brix contents. The computer can normalize the AP spectral data prior to comparing the AP spectral data with the reference spectral data.

In step 1140, the computer generates an output signal that corresponds to the result of the comparison from step 1130. The output signal can include encoded data that can be displayed on a computer display that is in electrical communication with the computer. Additionally or alternatively, the encoded data can be sent wirelessly to a handheld device, such as a smartphone, that can display the data on the handheld device's display.

In addition or in the alternative, the output signal can include a product sort output signal that can cause a product sorter (e.g., in electrical communication with the computer) to discard the agricultural product (e.g., when the quality condition is poor) or to take other action with respect to the agricultural product. The product sorter can be the same as or different than product sorter 310. For example, the product sorter can move the agricultural product to a different conveyor belt or to a different container. In a specific embodiment, when the agricultural product is an orange (e.g., navel orange) and the quality condition is Brix content, the product sorter can perform a first action when the measured Brix content is greater than or equal to a minimum or threshold Brix content and can perform a second action when the measured Brix content is below the minimum or threshold Brix content. For example, the product sorter can discard the orange when the when the measured Brix content is below the minimum or threshold Brix content. In another example, the product sorter can move the orange to a different conveyor belt or to a container when the measured Brix content is greater than or equal to the minimum or threshold Brix content. Other actions or inactions can be taken for other quality conditions and/or for other agricultural products.

In addition or in the alternative, the output signal can include a product sort output signal that can cause a product sorter (e.g., in electrical communication with the computer) to sort the agricultural product based on the measured quality condition. The product sorter can be the same as or different than product sorter 310. For example, the product sorter can move the agricultural product to a dedicated conveyor belt or to a dedicated container for each quality grade (e.g., poor, low, better, and best). In a specific embodiment, when the agricultural product is an orange (e.g., navel orange) and the quality condition is Brix content, the product sorter can perform a first action (e.g., placing the product on a first conveyor belt or in a first container) when the measured Brix content is between 0 and a first threshold Brix content (e.g., 9), which can correspond to a poor quality grade. The product sorter can perform a second action (e.g., placing the product on a second conveyor belt or in a second container) when the measured Brix content is between the first threshold Brix content (e.g., 9) and a second threshold Brix content (e.g., 11), which can correspond to a low quality grade. The product sorter can perform a third action (e.g., placing the product on a third conveyor belt or in a third container) when the measured Brix content is between the second threshold Brix content (e.g., 11) and a third threshold Brix content (e.g., 12), which can correspond to a better quality grade. The product sorter can perform a fourth action (e.g., placing the product on fourth third conveyor belt or in a fourth container) when the measured Brix content is between the third threshold Brix content (e.g., 12) and a fourth threshold Brix content (e.g., 14), which can correspond to a best quality grade.

In addition or in the alternative, when the agricultural product is an orange and the quality condition is limonin content, the product sorter can perform a first action (e.g., placing the product on a first conveyor belt or in a first container) when the measured limonin content is between a first threshold limonin content (e.g., 5) and a second threshold limonin content (e.g., 4), which can correspond to a poor quality grade. The product sorter can perform a second action (e.g., placing the product on a second conveyor belt or in a second container) when the measured limonin content is between the second threshold limonin content (e.g., 4) and a third threshold limonin content (e.g., 3), which can correspond to a low quality grade. The product sorter can perform a third action (e.g., placing the product on a third conveyor belt or in a third container) when the measured limonin content is between the third threshold limonin content (e.g., 3) and a fourth threshold limonin content (e.g., 2), which can correspond to a better quality grade. The product sorter can perform a fourth action (e.g., placing the product on fourth third conveyor belt or in a fourth container) when the measured limonin content is between the fourth threshold limonin content (e.g., 2) and a fifth threshold limonin content (e.g., 1), which can correspond to a best quality grade.

In some embodiments, the method can include 1100 can include performing one or more calibrations of the quality detection apparatus (e.g., spectrometer or spectrograph). A first calibration can include capturing a dark reference by recording first spectral scan data with the sensor light ingress port closed (i.e., shutter closed). This effectively records a noise floor that can be subtracted from later data to reduce the influence of sensor variation, which can occur due to change in ambient temperature or component damage or aging.

A second calibration can include capturing a white reference by recording second spectral scan data with the sensor FOV filled by a white, highly reflective target. This white reference second spectral scan data represents the instantaneous system performance with a near-perfect reflectance from the target. The white reference second spectral scan data can be used to effectively normalize or scale subsequent data sets of agricultural product samples. For example, the external ambient conditions change often in practical agricultural product quality assessment scenarios. For example, the position of the sun in the sky can impact the illumination of the sample area. This may be true even when artificial lighting is used, since there will still be some illumination contribution from sunlight in any outdoor scenario, or even an indoor scenario with facility windows.

A third calibration can include capturing samples of the agricultural product to be scanned. For example, the agricultural products can vary between harvest seasons and this calibration can be used to account for those differences. In a specific example, if the weather one year produces much lower quality agricultural products, but a grower still desires to sort into low, medium or high quality based on the overall conditions, the model can be fine-tuned with new regression values. In addition, the same quality detection apparatus or system may be employed to analyze two distinct varieties of oranges (e.g., Hamlin and Valencia) during their respective harvest seasons, then to analyze tomatoes or grapes during other seasons. Each specific agricultural product variety may require a distinct software model for evaluation. In addition, several models may be desired to run somewhat simultaneously for any given agricultural product variety.

Figure 12:
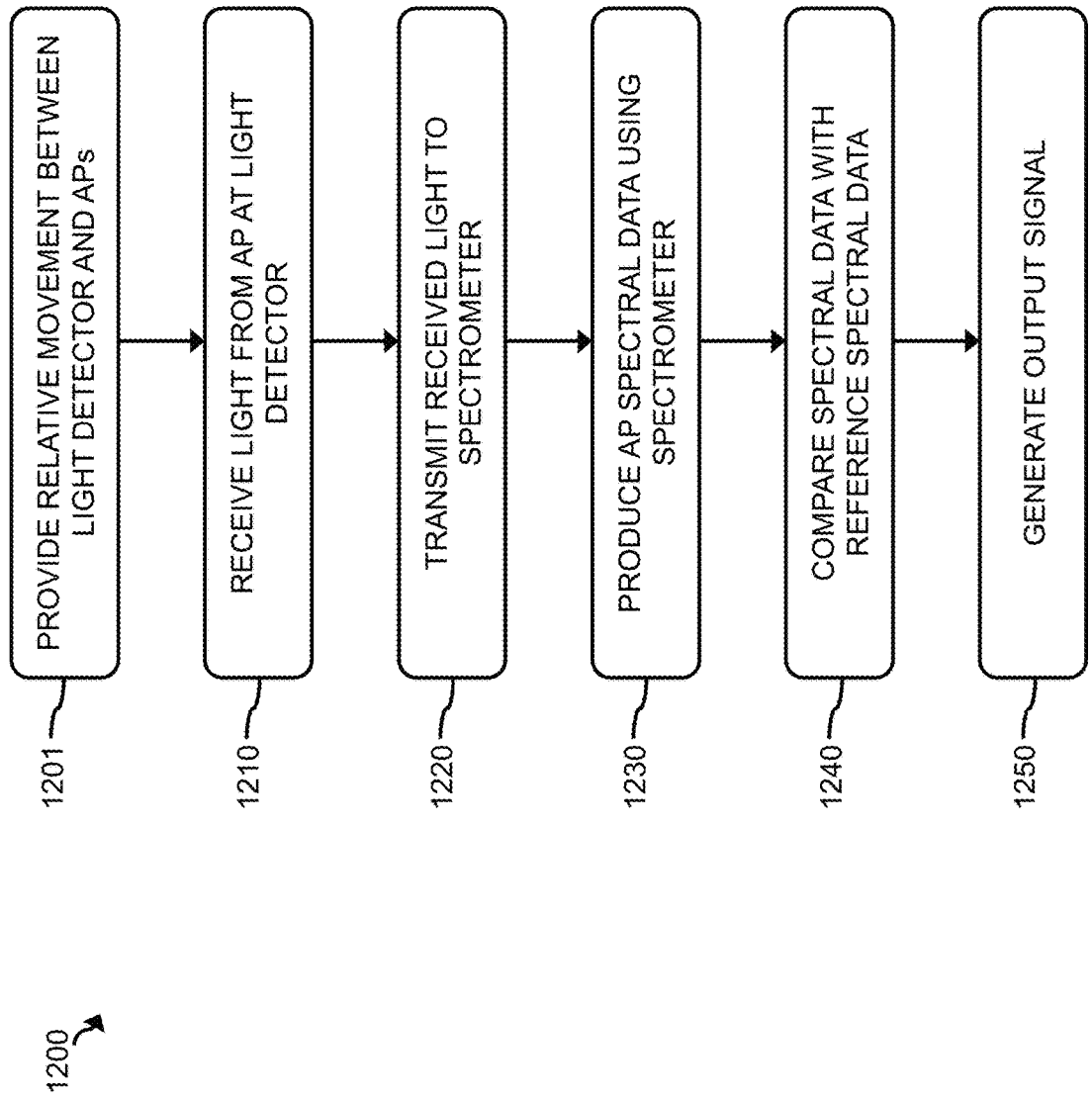
FIG. 12 is a flow chart of a method for determining a quality condition of a plurality of agricultural products according to an embodiment.

FIG. 12 is a flow chart of a method 1200 for determining a quality condition of a plurality of agricultural products according to an embodiment. Method 1200 can be performed with any of the apparatus and systems described herein. In step 1201, relative movement is provided between a light detector and the agricultural products. In one embodiment, the light detector is stationary and the agricultural products are located in an open bed of a truck, such as open bed 142. The truck can pull the agricultural products in the open bed during this step. In another embodiment, the light detector is stationary and the agricultural products are located on a conveyor belt that moves the agricultural products, such as along a production or sorting line. In other embodiments, the agricultural products are stationary and the light detector moves with respect to the agricultural products. For example, the light detector can move along the length of the truck to scan the agricultural products in the truck's open bed. In another example, the light detector can move over (e.g., in an aerial vehicle such as a drone or airplane) the agricultural products in the field (e.g., prior to or after they are picked or harvested). The light detector can be located next to or physically coupled with a light or light source, in which case relative movement is provided between the (a) agricultural products and (b) the light detector and light/light source.

In step 1210, light or a light image is received at a light detector. The received light or light image includes scattered, refracted, and/or reflected light from the agricultural products. The light can be received from only one agricultural product at a time or from multiple agricultural products simultaneously.

In step 1220, the received light is transmitted to a spectrometer, which can be the same as spectrometer 520, 70. In step 1230, the spectrometer produces AP spectral data (e.g., spectral scan data 1700) of the received light. The AP spectral data can include the measured intensity of the light at each of a plurality of wavelengths.

In step 1240, the AP spectral data is sent to a computer that is in electrical communication with the spectrometer. The computer compares the AP spectral data with reference spectral data of the agricultural product. The reference spectral data can correspond to agricultural products having known quality conditions. The reference spectral data is for the same type, variety, and/or species of agricultural product as the agricultural product from which the light is received in step 1210. For example, when the agricultural products from which the light is received in step 1210 are navel oranges, the reference spectral data is also for navel oranges having known quality conditions. The computer can normalize (or otherwise scale) the AP spectral data prior to comparing the AP spectral data with the reference spectral data.

In step 1250, the computer generates an output signal that corresponds to the result of the comparison from step 1240. The output signal can include encoded data that can be displayed on a computer display that is in electrical communication with the computer. Additionally or alternatively, the encoded data can be sent wirelessly to a handheld device, such as a smartphone, that can display the data on the handheld device's display.

In addition or in the alternative, the computer can send a product sort output signal to a product sorter that can cause the product sorter to discard the agricultural product (e.g., when the quality condition is poor) or to take other action with respect to the agricultural product. The product sorter can be the same as or different than product sorter 310. For example, the product sorter can move the agricultural product to a different conveyor belt or to a different container, for example as discussed above with respect to step 1140.

In addition or in the alternative, the computer can send a gate control signal to a gate (e.g., gate 170) that can cause the gate to open or close. The opened or closed gate can direct a vehicle along a first pathway and/or close a second pathway for a vehicle to travel, the vehicle transporting the agricultural products. For example, when the quality condition is good (e.g., the measured Brix content of an orange is greater than or equal to a minimum or threshold Brix content), the vehicle can transport the agricultural products to a processing location or a holding location. When the quality condition is poor (e.g., the measured Brix content of an orange is less than a minimum or threshold Brix content), the vehicle can discard the agricultural product.

In addition or in the alternative, the gate control signal can be used to sort the agricultural product based on the measured quality condition. For example, the gate control signal can indicate each quality grade (e.g., poor, low, better, and best). In a specific embodiment, when the agricultural product is an orange (e.g., navel orange) and the quality condition is Brix content, the gate control signal can include a first audible and/or a first visual output signal when the measured Brix content is between 0 and a first threshold Brix content (e.g., 9), which can correspond to a poor quality grade. Additionally or alternatively, the gate control signal can cause a first gate to open when the measured Brix content is between 0 and the first threshold Brix content. The gate control signal can include a second audible and/or a second visual output signal when the measured Brix content is between the first threshold Brix content (e.g., 9) and a second threshold Brix content (e.g., 11), which can correspond to a low quality grade. Additionally or alternatively, the gate control signal can cause a second gate to open when the measured Brix content is the first and second threshold Brix contents. The gate control signal can include a third audible and/or a third visual output signal when the measured Brix content is between the second threshold Brix content (e.g., 11) and a third threshold Brix content (e.g., 12), which can correspond to a better quality grade. Additionally or alternatively, the gate control signal can cause a third gate to open when the measured Brix content is the second and third threshold Brix contents. The gate control signal can include a fourth audible and/or a fourth visual output signal when the measured Brix content is between the third threshold Brix content (e.g., 12) and a fourth threshold Brix content (e.g., 14), which can correspond to a best quality grade. Additionally or alternatively, the gate control signal can cause a fourth gate to open when the measured Brix content is the third and fourth threshold Brix contents.

In addition or in the alternative, when the agricultural product is an orange (e.g., navel orange) and the quality condition is limonin content, the gate control signal can include a first audible and/or a first visual output signal when the measured limonin content is between a first threshold limonin content (e.g., 5) and a second threshold limonin content (e.g., 4), which can correspond to a poor quality grade. Additionally or alternatively, the gate control signal can cause a first gate to open when the measured limonin content is between the first and second threshold limonin contents. The gate control signal can include a second audible and/or a second visual output signal when the measured limonin content is between the second threshold limonin content (e.g., 4) and a third threshold limonin content (e.g., 3), which can correspond to a low quality grade. Additionally or alternatively, the gate control signal can cause a second gate to open when the measured limonin content is between the second and third threshold limonin contents. The gate control signal can include a third audible and/or a third visual output signal when the measured limonin content is between the third threshold limonin content (e.g., 3) and a fourth threshold limonin content (e.g., 2), which can correspond to a better quality grade. Additionally or alternatively, the gate control signal can cause a third gate to open when the measured limonin content is between the third and fourth threshold limonin contents. The gate control signal can include a fourth audible and/or a fourth visual output signal when the measured limonin content is between the fourth threshold limonin content (e.g., 2) and a fifth threshold limonin content (e.g., 1), which can correspond to a best quality grade. Additionally or alternatively, the gate control signal can cause a fourth gate to open when the measured limonin content is between the fourth and fifth threshold limonin contents.

In some embodiments, the quality condition can be averaged for multiple images of the agricultural products. For example, when the agricultural products are stored in the open bed of a truck, the light can be received at the light detector for multiple agricultural products along the length of the open bed. The number of light images received by the light detector can be a function of the relative speed of the vehicle with respect to the light detector. The quality condition, which can be quantitative, can be averaged over the number of light images collected. For example, when the agricultural products are navel oranges and the quality condition is Brix, each light image can correspond to a respective Brix measurement, which can be averaged based on the number of light images/Brix measurements. The output signal, including the product sort output signal and the gate control signal, can be based on an average quality condition, such as an average Brix measurement. In some embodiments, the quality condition and/or average quality condition can be used to estimate a valuation of the agricultural products. For example, the estimated value of a truckload of oranges can be determined based on an average Brix measurement of at least the exposed oranges in the truck.

Figure 13:
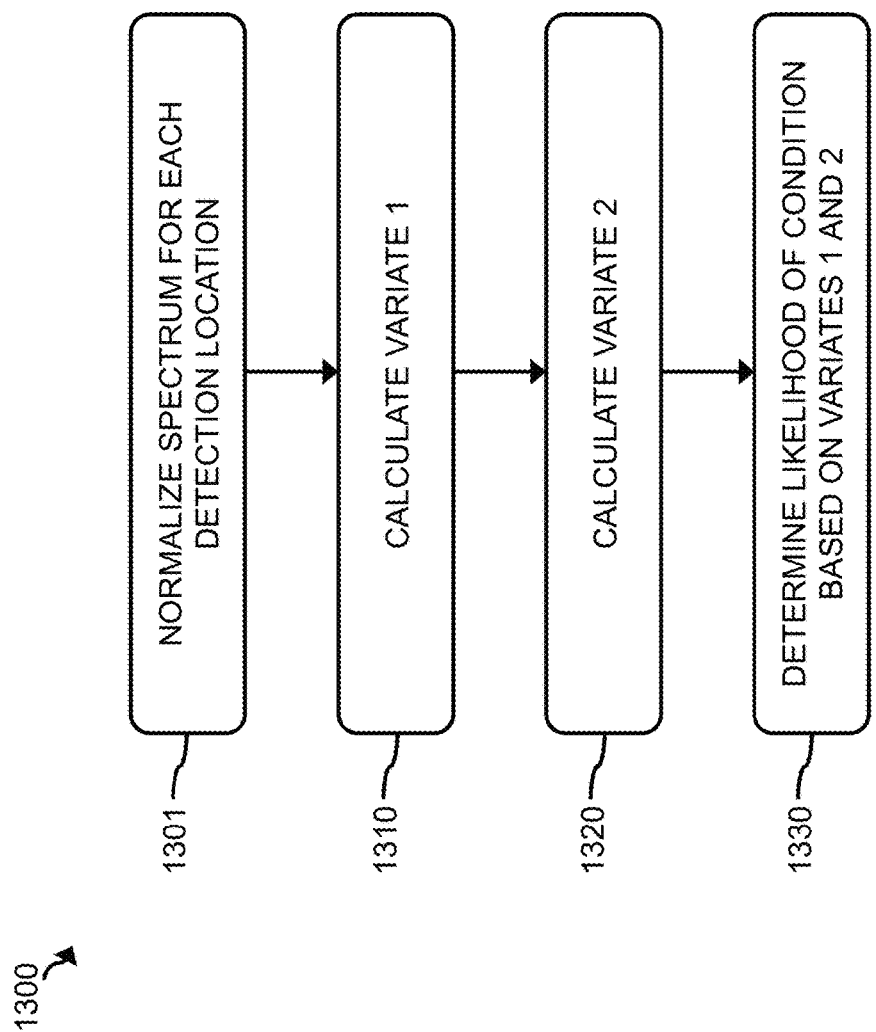
FIG. 13 is a flow chart for a computer-implemented method for analyzing spectral scan data of a target agricultural product.

FIG. 13 is a flow chart 1300 for a computer-implemented method for analyzing spectral scan data of a target agricultural product that is simultaneously collected from multiple detection locations (e.g., relative distances from a light output) to determine if the target agricultural product has or is likely to have a quality condition, such as a disease or a predetermined Brix content. In some embodiments, the flow chart 1300 can correspond to the comparing step 1130, 1240, discussed above.

In step 1301, the spectrum for each detection location is normalized to unity. In one example, the spectrum for each detection location can be normalized based on the maximum intensity in the respective spectrum. In another example, the spectrum for each detection location can be normalized based on the mean or median maximum intensity of the scan in the respective spectrum. In some examples, the spectrum can be scaled to reduce the effects of illumination spectra and/or ambient conditions, thereby converting from radiance to reflectance. The scaling curve can be produced by recording a "white reference" (e.g., second calibration data) just prior to collecting spectra for the agricultural product. Those skilled art will recognize that other methods of normalization (or scaling) can be applied to the spectra.

In step 1310, a first variate (V1) is calculated. V1 is defined as the area between the normalized spectra at a first detection location or distance (i.e., from the light output) and at a second detection location or distance (i.e., from the light output) over a predetermined wavelength range. In some embodiments, the first detection location is about 5 mm, about 10 mm, or about 15 mm from the light output and the second detection location is about 10 mm, about 15 mm, or about 20 mm from the light output. In a specific example, the first detection location is about 5 mm from the light output and the second detection location is about 10 mm, about 15 mm, or about 20 mm from the light output. In another specific example, the first detection location is about 10 mm from the light output and the second detection location is about 15 mm or about 20 mm from the light output. In a specific example, the first detection location is about 15 mm from the light output and the second detection location is about 20 mm from the light output. Those skilled in the art will recognize that the first detection location and/or the second detection location can be another distance from the light output. In other embodiments, the first and second detection locations can range from millimeters to meters and/or to kilometers depending on the application.

Figure 14:
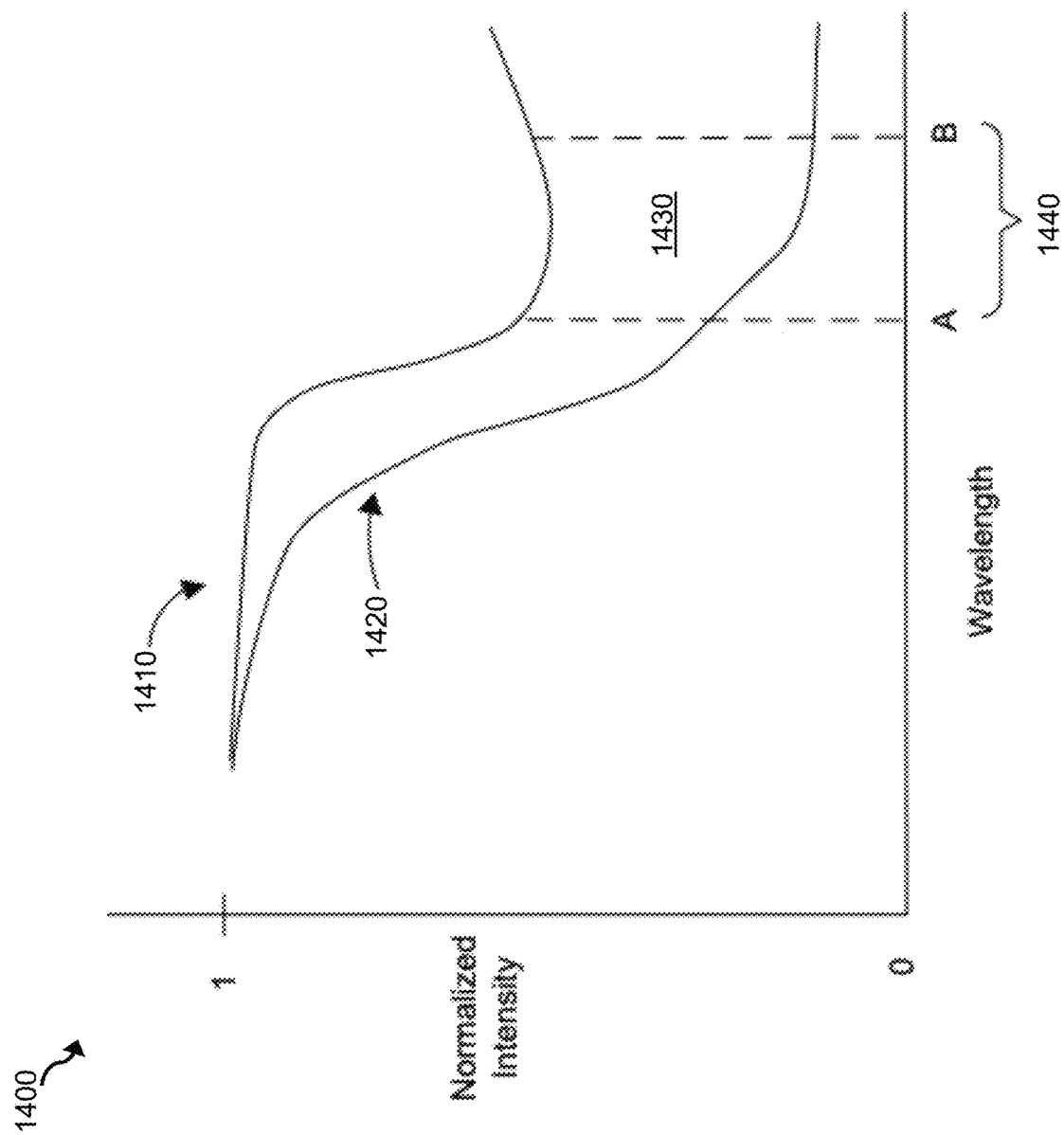
FIGS. 14 and 15 are example graphs that illustrate the method of FIG. 13.

An example of this area calculated for the first variate (V1) is illustrated in graph 1400 in FIG. 14. Graph 1400 includes a first normalized spectrum 1410 for a first detection location or distance and a second normalized spectrum 1420 for a second detection location or distance. The area 1430 calculated for the first variate (V1) is between the first and second normalized spectra 1410, 1420 over the predetermined wavelength range 1440 (i.e., from wavelength A to wavelength B). The first and second locations or distances corresponding to the first normalized spectrum 1410 and the second normalized spectrum 1420 can be any of the locations or distances discussed herein, such as those discussed with respect to step 1310.

Returning to FIG. 13, a second variate (V2) is calculated in step 1320. V2 is defined as the area between the normalized spectra at a second detection location or distance (i.e., from the light output) and at a third detection location or distance (i.e., from the light output) over a predetermined wavelength range. In some embodiments, the second detection location/distance and/or the third detection location/ distance is/are about 5 mm, about 10 mm, about 15 mm, about 20 mm, any distance between any two of the foregoing distances, or another distance. In a specific example, the second detection location/distance is about 20 mm from the light output and the third detection location/distance is about 15 mm. Those skilled in the art will recognize that the first detection location and/or the second detection location can be another distance from the light output. In other embodiments, the third detection locations can range from millimeters to meters and/or to kilometers depending on the application. The predetermined wavelength range can be the same or different than the predetermined wavelength range discussed about with respect to step 1310 and/or graph 1400. In addition, those skilled in the art will recognize that different predetermined wavelength ranges can be used to calculate V1 and/or V2.

Figure 15:
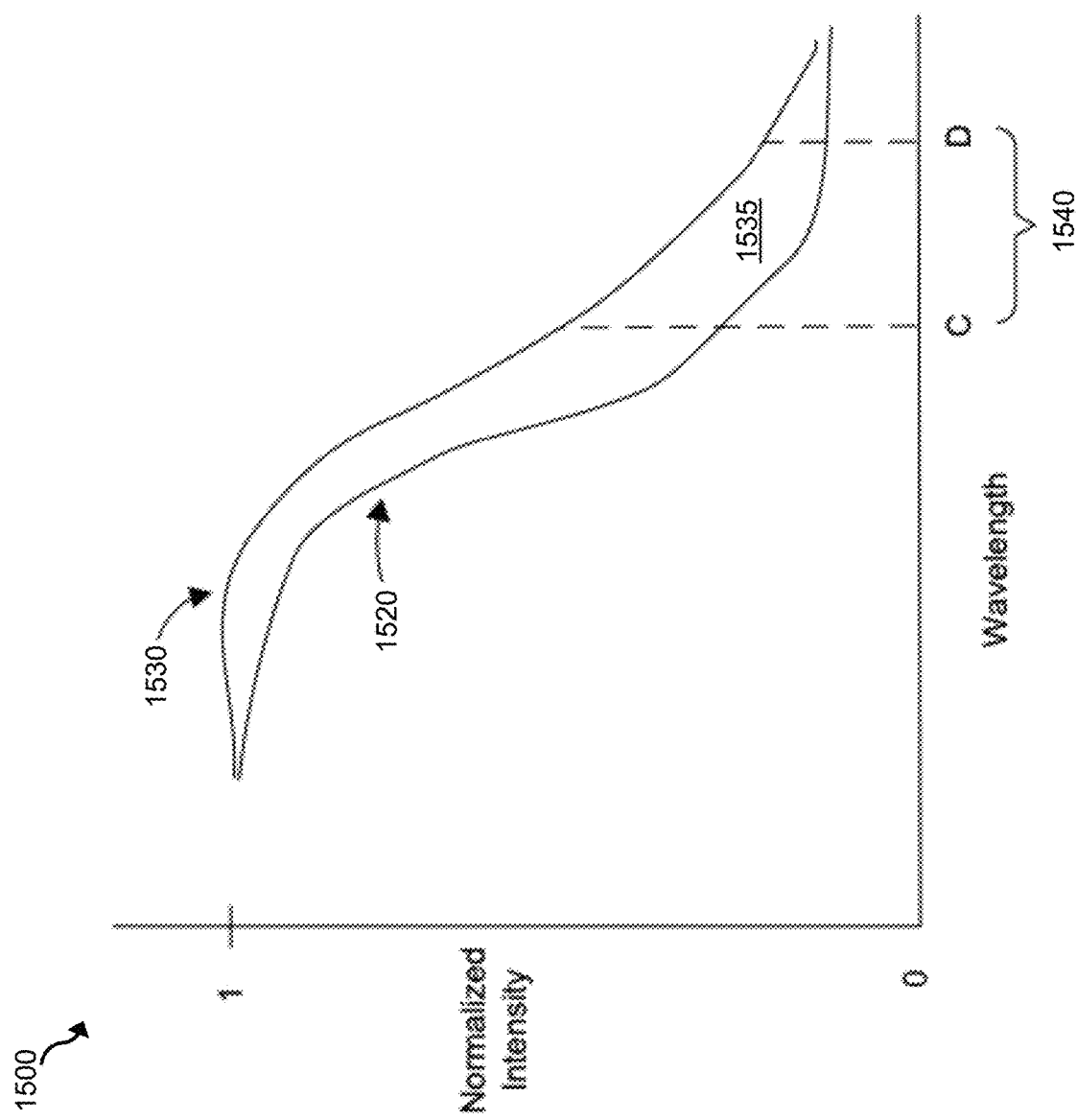

An example of this area calculated for the second variate (V2) is illustrated in graph 1500 in FIG. 15. Graph 1500 includes a second normalized spectrum 1520 for a second detection distance and a third normalized spectrum 1530 for a third detection distance. The second normalized spectrum 1520 can be the same as the second normalized spectrum 1420. The area 1535 calculated for the second variate (V2) is between the second and third normalized spectra 1520, 1530 over the predetermined wavelength range 1540 (i.e., from wavelength C to wavelength D). Wavelengths C and/or D can be the same as or different than wavelengths A and B, respectively, discussed above with respect to Graph 1400. The second and third detection locations/distances can be the same as or different than the second and third detection locations/distances discussed above with respect to step 1320. In a specific embodiment, the second and third detection locations/distances are about 20 mm from the light output and about 15 mm from the light output, respectively. Those skilled in the art will recognize that other detection locations/distances can be used to calculate the second variate.

Returning to FIG. 13, in step 1330, the likelihood that the target agricultural product has a quality condition, such a disease or a given Brix content, is determined based on V1 and V2. In one example, the target agricultural product's values for V1 and V2 are compared to a plot of the values for V1 and V2 that were calculated for a first agricultural product (or first agricultural product group) that is known to have a first quality condition (e.g., diseased) and for a second agricultural product (or second agricultural product group) that is known to have a second quality condition (e.g., have a given Brix content).

If the target agricultural product's V1 and V2 values are statistically close to the second agricultural product or agricultural product group's V1 and V2 values, it is likely that the target agricultural product has the second quality condition. If the target agricultural product's V1 and V2 values are statistically close to the first agricultural product or agricultural product group's V1 and V2 values, it is unlikely that the target agricultural product has the first quality condition. If the target agricultural product's V1 and V2 values are not statistically close to the first or second agricultural product or group's V1 and V2 values, it is uncertain whether the target agricultural product has the first or second quality condition, and therefore additional testing or inspection may be needed.

The present invention should not be considered limited to the particular embodiments described above. Various modifications, equivalent processes, as well as numerous structures to which the present invention may be applicable, will be readily apparent to those skilled in the art to which the present invention is directed upon review of the present disclosure. The above-described embodiments may be implemented in numerous ways. One or more aspects and embodiments involving the performance of processes or methods may utilize program instructions executable by a device (e.g., a computer, a processor, or other device) to perform, or control performance of, the processes or methods.

In this respect, various inventive concepts may be embodied as a non-transitory computer readable storage medium (or multiple non-transitory computer readable storage media) (e.g., a computer memory of any suitable type including transitory or non-transitory digital storage units, circuit configurations in Field Programmable Gate Arrays or other semiconductor devices, or other tangible computer storage medium) encoded with one or more programs that, when executed on one or more computers or other processors, perform methods that implement one or more of the various embodiments described above. When implemented in software (e.g., as an app), the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more communication devices, which may be used to interconnect the computer to one or more other devices and/or systems, such as, for example, one or more networks in any suitable form, including a local area network or a wide area network, such as an enterprise network, and intelligent network (IN) or the Internet. Such networks may be based on any suitable technology and may operate according to any suitable protocol and may include wireless networks or wired networks.

Also, a computer may have one or more input devices and/or one or more output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

The non-transitory computer readable medium or media may be transportable, such that the program or programs stored thereon may be loaded onto one or more different computers or other processors to implement various one or more of the aspects described above. In some embodiments, computer readable media may be non-transitory media.

The terms "program," "app," and "software" are used herein in a generic sense to refer to any type of computer code or set of computer-executable instructions that may be employed to program a computer or other processor to implement various aspects as described above. Additionally, it should be appreciated that, according to one aspect, one or more computer programs that when executed perform methods of the present application need not reside on a single computer or processor but may be distributed in a modular fashion among a number of different computers or processors to implement various aspects of the present application.

Computer-executable instructions may be in many forms, such as program modules, executed by one or more computers or other devices. Generally, program modules include routines, programs, objects, components, data structures, etc. that performs particular tasks or implement particular abstract data types. The functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Thus, the present disclosure and claims include new and novel improvements to existing methods and technologies, which were not previously known nor implemented to achieve the useful results described above. Users of the present method and system will reap tangible benefits from the functions now made possible on account of the specific modifications described herein causing the effects in the system and its outputs to its users. It is expected that significantly improved operations can be achieved upon implementation of the claimed invention, using the technical components recited herein.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

What is claimed is:

1. A method for sorting an agricultural product, comprising:
    providing a relative movement between a light detector and a plurality of agricultural products disposed in a container in a vehicle;
    receiving a received light at a light detector, the received light comprising reflected, scattered, refracted, and/or deflected light from the agricultural product;
    transmitting the received light to a spectrometer;
    producing AP spectral data of the received light using the spectrometer;
    in a computer in electrical communication with the spectrometer, comparing the AP spectral data to reference spectral data to determine whether the agricultural products have a quality condition, the reference spectral data corresponding to known quality conditions of the agricultural product;
    when the exposed agricultural product has the quality condition:
        sending an output signal to an automated product sorter; and
        activating a gate to provide or restrict access to a direction of travel for the vehicle.

2. The method of claim 1, wherein:
the agricultural products comprise oranges, and
the quality condition comprises a minimum Brix content of each orange.

3. The method of claim 1, wherein:
the agricultural products comprise oranges, and the quality condition comprises a minimum average Brix content of the oranges.

4. The method of claim 1, wherein the vehicle drives while the received light is received at the light detector.

5. The method of claim 1, wherein the agricultural product is in vivo when the received light is received at the light detector.

6. The method of claim 1, wherein the agricultural product has been harvested when the received light is received at the light detector.

7. The method of claim 1, wherein the agricultural product is illuminated by sunlight and/or moonlight.

8. The method of claim 1, further comprising illuminating the agricultural product with an artificial light produced by a halogen lamp, a light emitting diode, a laser, and/or a supercontinuum light source.

\* \* \* \* \*